United States Patent
Bentzien et al.

(10) Patent No.: US 9,828,364 B2
(45) Date of Patent: Nov. 28, 2017

(54) PYRAZOLE COMPOUNDS AS BTK INHIBITORS

(71) Applicant: Boehringer Ingelheim International GmbH, Ingelheim am Rhein (DE)

(72) Inventors: Joerg Bentzien, White Plains, NY (US); Angela Kay Berry, Gaylordsville, CT (US); Todd Bosanac, New Milford, CT (US); Michael Jason Burke, Newtown, CT (US); Darren Todd Disalvo, New Milford, CT (US); Can Mao, Philadelphia, PA (US); Wang Mao, Milford, CT (US); Yue Shen, Berlin, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/114,923

(22) PCT Filed: Jan. 23, 2015

(86) PCT No.: PCT/US2015/012590
§ 371 (c)(1),
(2) Date: Jul. 28, 2016

(87) PCT Pub. No.: WO2015/116485
PCT Pub. Date: Aug. 6, 2015

(65) Prior Publication Data
US 2016/0340339 A1   Nov. 24, 2016

Related U.S. Application Data

(60) Provisional application No. 61/932,913, filed on Jan. 29, 2014.

(51) Int. Cl.
| C07D 403/04 | (2006.01) |
| C07D 401/04 | (2006.01) |
| C07D 401/10 | (2006.01) |
| C07D 403/10 | (2006.01) |

(52) U.S. Cl.
CPC ......... C07D 403/04 (2013.01); C07D 401/04 (2013.01); C07D 401/10 (2013.01); C07D 403/10 (2013.01)

(58) Field of Classification Search
CPC ............................ C07D 403/04; C07D 401/04
USPC .................................................. 514/210.18
See application file for complete search history.

(56) References Cited

U.S. PATENT DOCUMENTS

| 7,560,571 | B2 | 7/2009 | Ronan et al. |
| 8,377,946 | B1 | 2/2013 | Chen et al. |
| 8,557,803 | B2 | 10/2013 | Yamamoto et al. |
| 2004/0198986 | A1 | 10/2004 | Adams et al. |
| 2008/0045542 | A1 | 2/2008 | Ronan et al. |
| 2008/0076921 | A1 | 3/2008 | Honigberg et al. |
| 2009/0012309 | A1 | 1/2009 | Adams et al. |
| 2011/0003806 | A1 | 1/2011 | Hirose et al. |
| 2014/0045813 | A1* | 2/2014 | Bentzien ............... C07D 231/14 514/210.18 |
| 2016/0340339 | A1 | 11/2016 | Bentzien et al. |

FOREIGN PATENT DOCUMENTS

| CA | 2784647 A1 | 7/2011 |
| EP | 2543375 A1 | 1/2013 |
| WO | 199740019 A1 | 10/1997 |
| WO | 2003015776 A1 | 2/2003 |
| WO | 2007117692 A2 | 10/2007 |
| WO | 2008039218 A2 | 4/2008 |
| WO | 2008121742 A2 | 10/2008 |
| WO | 201012690 A1 | 2/2010 |
| WO | 2010055304 A2 | 5/2010 |
| WO | 2010090716 A1 | 8/2010 |
| WO | 2011082732 A1 | 7/2011 |
| WO | 2011152351 A1 | 12/2011 |
| WO | 2012021615 A1 | 2/2012 |
| WO | 2013113097 A1 | 8/2013 |
| WO | 2014025976 A1 | 2/2014 |
| WO | WO 2014025976 A1 * | 2/2014 ........... C07D 231/14 |

(Continued)

OTHER PUBLICATIONS

International Search Report for PCT/US2015/012590 maled on Mar. 25, 2015.
Abstract in English for WO 2011/082732, publication date Jul. 14, 2011.
Akinleye, A. et al., "Ibrutinib and novel BTK inhibitors in clinical deveolopment." Journal of Hematology & Oncology, 2013, 6:59, pp. 1-9.
Chakravarty, S. et al., "Kinase inhibitors: A new tool for the treatment of rheumatoid arthritis." Clinical Immunology, 2013, vol. 148, pp. 66-78.
International Search Report and Written Opinion for PCT/US2013/054096 dated Sep. 30, 2013.

(Continued)

*Primary Examiner* — Yong Chu
(74) *Attorney, Agent, or Firm* — Marc A. Began; Atabak R. Royaee

(57) ABSTRACT

The present invention encompasses compounds of the formula (I) wherein the groups $R_1$, Cy, and Y are defined herein, which are suitable for the treatment of diseases related to BTK, process of making, pharmaceutical preparations which contain compounds and their methods of use.

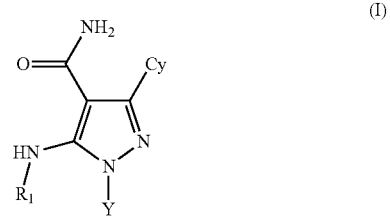

(I)

7 Claims, No Drawings

(56) References Cited

FOREIGN PATENT DOCUMENTS

WO  2014068527 A1  5/2014
WO  2014082598 A1  6/2014

OTHER PUBLICATIONS

International Search Report and Written Opinion for PCT/US2014/026113, dated Jun. 2, 2014.
International Search Report and Written Opinion for PCT/US2014/026966, dated Jul. 22, 2014.
Summary of Pfizer Oral Presentation, "Targeted covalent reversible inhibitors for Bruton's Tyrosine Kinase." Presented by Suvit Thaisrivongs on Apr. 16, 2013.
Whang, J. et al., "Bruton's tyrosine kinase inhibitors for the treatment of rheumatoid arthritis." Drug Discovery Today, 2014, pp. 1-5.
International Search Report PCT/US2016/066799 dated Jul. 12, 2017. 4 pgs.

* cited by examiner

PYRAZOLE COMPOUNDS AS BTK INHIBITORS

BACKGROUND OF THE INVENTION

1. Technical Field

The present invention relates to novel compounds which inhibit BTK and their use as medicaments.

2. Background Information

Members of the protein kinase family of human enzymes play important regulatory roles in a multitude of distinct signal transduction processes due to their post-translational modification of specific proteins via the addition of a phosphate group (Hunter, *Cell,* 1987 50, 823-829). Bruton's tyrosine kinase (BTK) is a member of the Tec family of tyrosine kinases and plays a critical role in B cell development, activation and antibody production.

The contribution of BTK to B cell biology is exemplified in the X-linked agammaglobulinemia (XLA) immunodeficiency in humans (reviewed in Lindvall, Immunol Rev 2005, 203, 200-215 that display attenuated calcium signaling upon BCR engagement, lack mature B cells in periphery due to block between pro- and pre-B cells stage and have lower levels of circulating antibodies than normal healthy subjects. The outcome of recent clinical trials with B cell depleting anti-CD20 molecules in diseases such as rheumatoid arthritis (RA) and multiple sclerosis (MS) support the hypothesis that B cells offer an important intervention node for controlling autoimmune disorders (Townsend et al. 2010). As such, attenuation of B cell activation and proliferation via inhibition of BTK may offer similar therapeutic benefit and is consistent with the demonstrated resistance of BTK-deficient mice to collagen induced arthritis (Jansson, 1993, Clin Exp Immunol 94, 459-465) and experimental autoimmune encephalitis (Svensson et al. 2002 and Mangla et al 2004). Similarly, the clinical efficacy observed with a neutralizing antibody to the B cell stimulating factor BlyS supports a role for B cells in the pathophysiology of systemic lupus erythematosus (SLE) (La Cava 2010). Given the necessity for BTK for the production of autoantibodies, including anti-DNA antibodies, in murine models of SLE (Steinberg et al., 1982; Golding et al., 1983; Scribner et al., 1987; Seldin et al., 1987; Satterthwaite et al., 1998; Takeshita et al., 1998; Whyburn et. al., 2003), BTK inhibitors may offer therapeutic benefit to SLE patients.

Within myeloid cells, BTK signal transduction is necessary for the stimulated release of inflammatory cytokines such as TNF from stimulated monocytes (Horwood, J Exp Med, 2003, 1603-1611) and for optimal actin cytoskeletal organization and lacunar bone resorption in isolated osteoclasts (Danks, 2011, J Bone and Mineral Research, 26, 182-192). Bone marrow derived mast cells lacking BTK exhibit impaired activation-induced degranulation and cytokine release (ref). Given the role of BTK in signal transduction processes across multiple cell types implicated in the pathogenesis of autoimmune and allergic disorders, inhibition of BTK activity may provide clinical benefit in diseases such as RA, MS, SLE, asthma and allergic disorders.

SUMMARY OF THE INVENTION

The invention comprises a novel class of heteroaromatic compounds and methods for making and using the same. These compounds are useful for the treatment of autoimmune and allergic disorders in that they exhibit good inhibitory effect upon BTK.

DETAILED DESCRIPTION OF THE INVENTION

In a first generic embodiment, there is provided a compound of the formula (I)

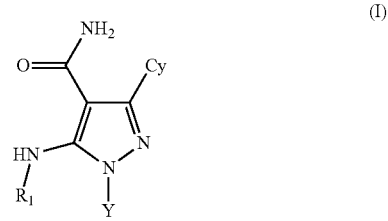

$R_1$ is H, $C_{1-4}$ alkyl;

Cy is chosen from

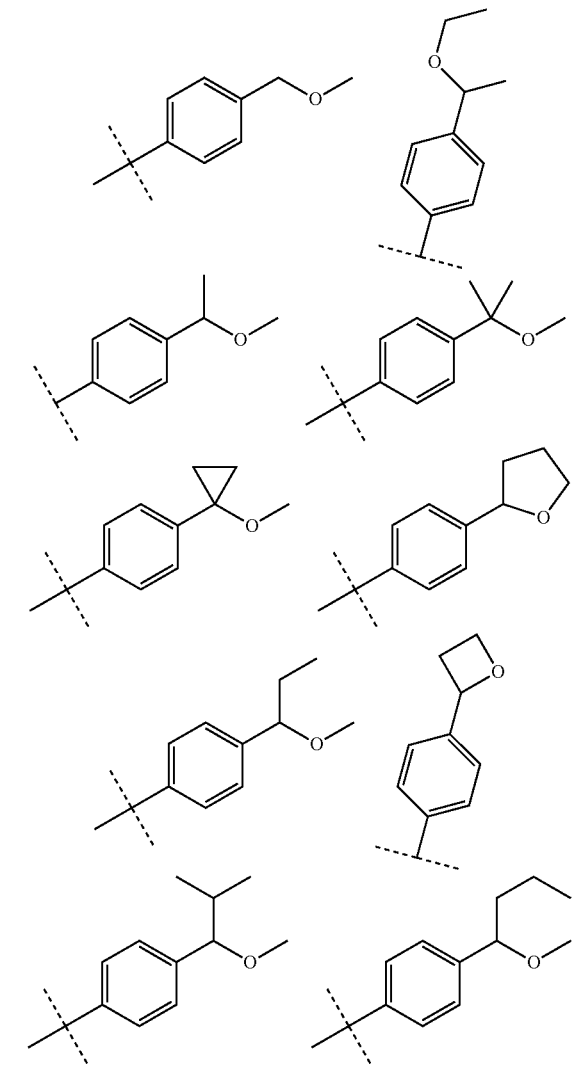

-continued
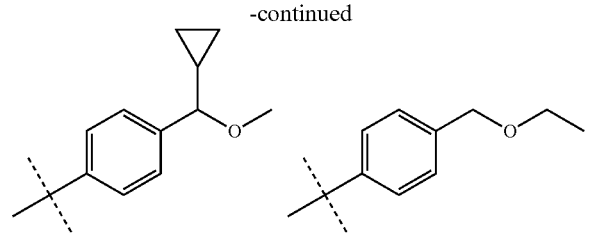
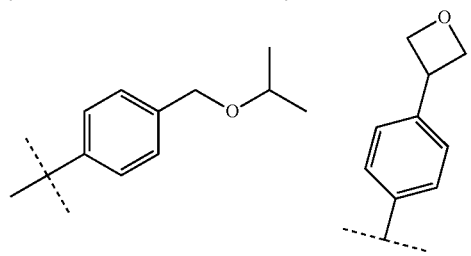
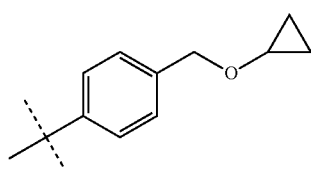
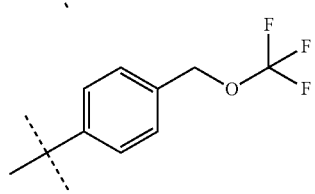
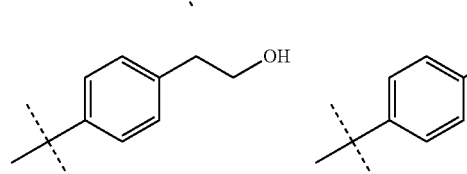
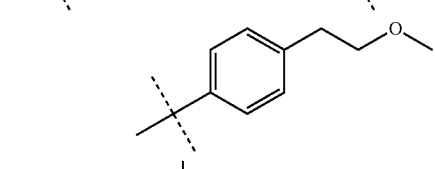
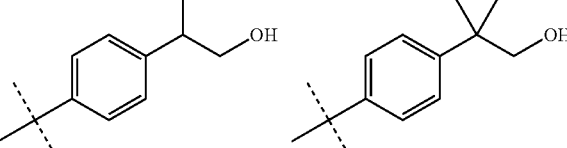
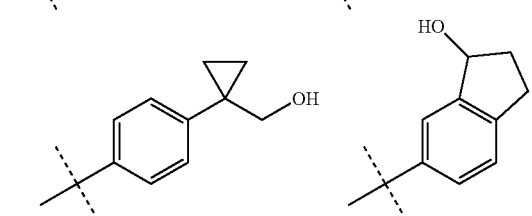
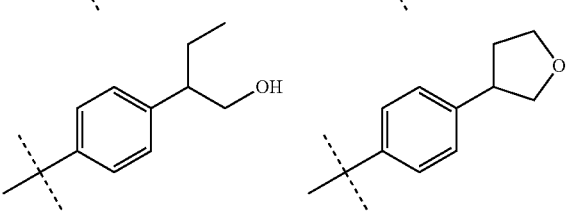
-continued
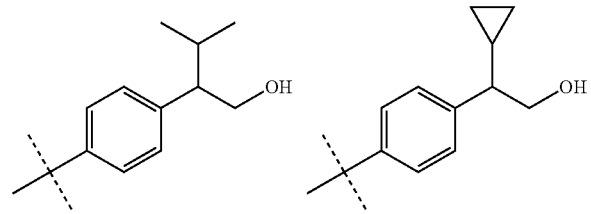
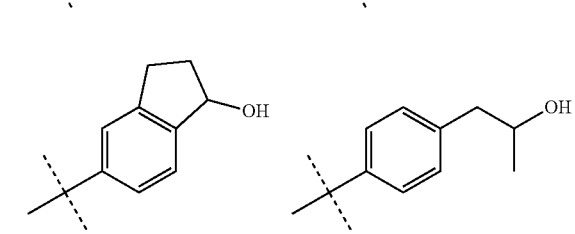
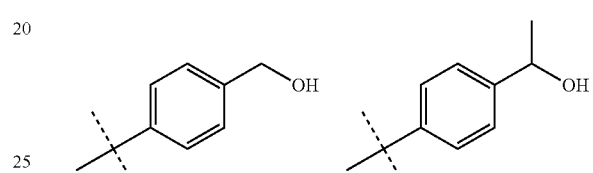
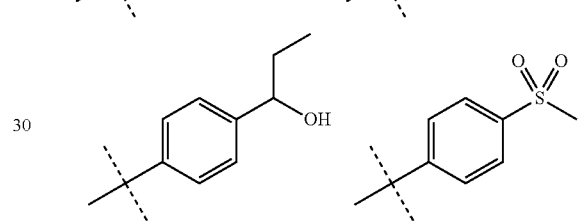
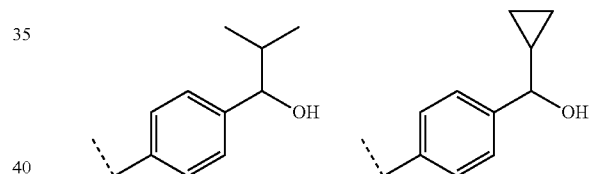
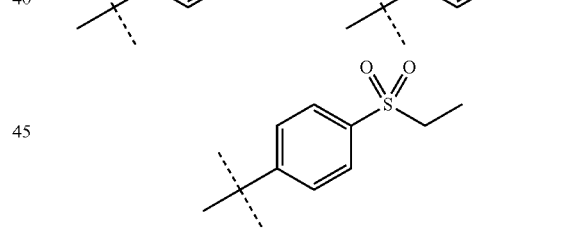
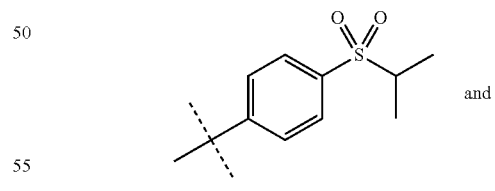
and
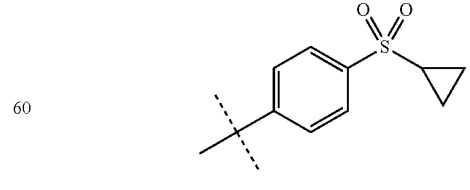
wherein each phenyl or attached substituent thereof can be optionally substituted by halogen, —CN, haloalkyl, methyl, methoxy, hydroxyl;

Y is a linker chosen from;

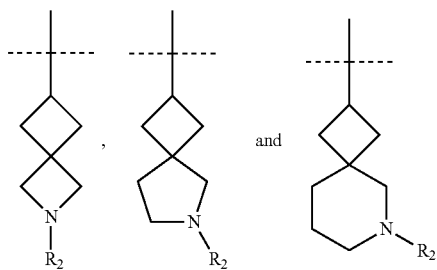

R₂ is chosen from

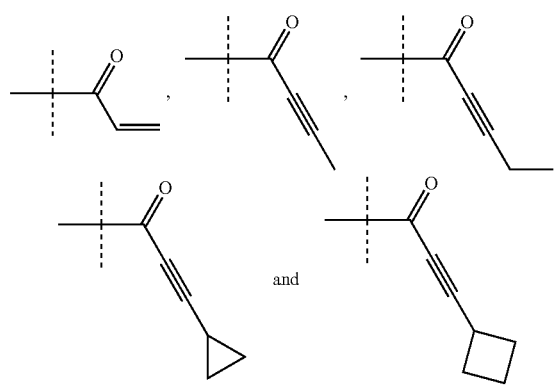

or a pharmaceutically acceptable salt thereof.

In a further embodiment, there is provided a compound of the formula (I) according to the embodiment herein-above and wherein The combination of Y and R2 is chosen from:

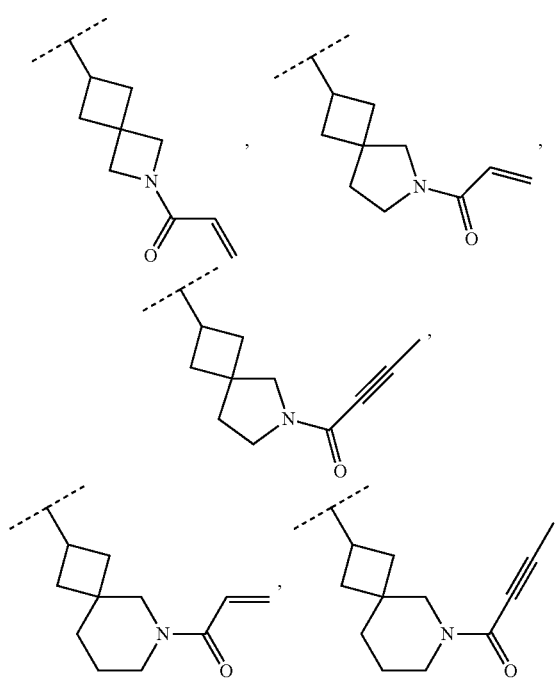

-continued

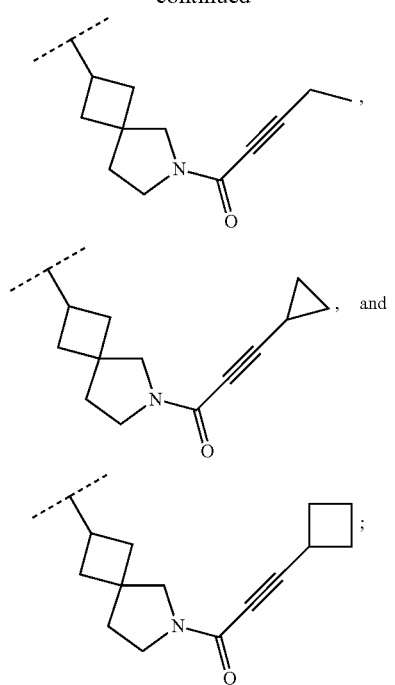

or a pharmaceutically acceptable salt thereof.

In a further embodiment, there is provided a compound of the formula (I) according to the embodiment herein-above and wherein Cy is chosen from

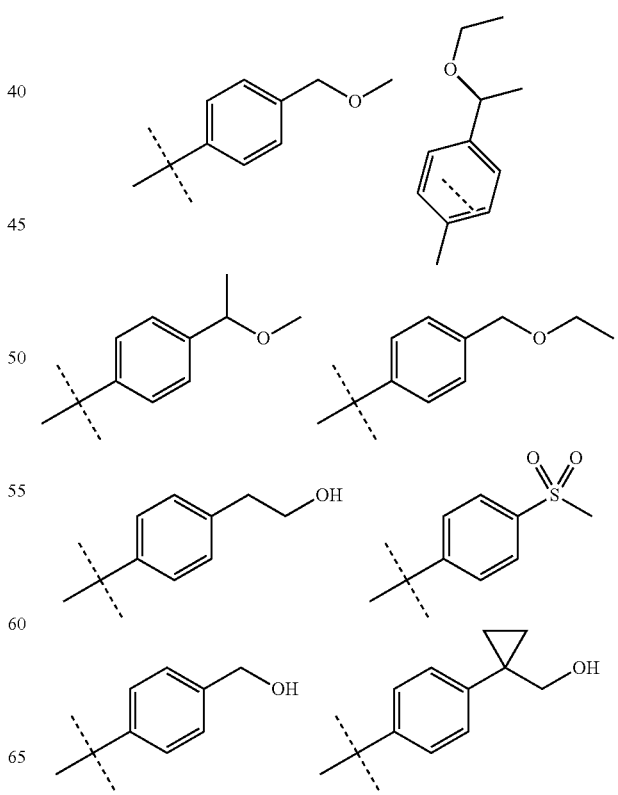

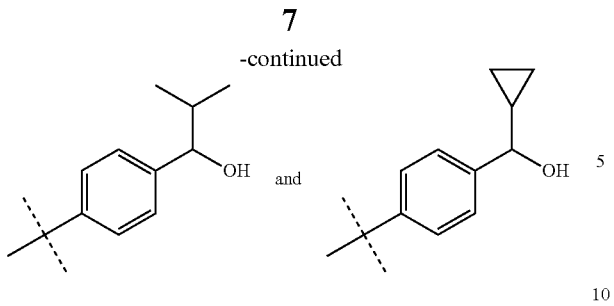  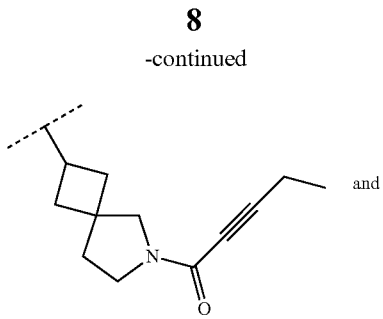

or a pharmaceutically acceptable salt thereof.

In a further embodiment, there is provided a compound of the formula (I) according to the embodiment herein-above and wherein The combination of Y and R2 is chosen from:

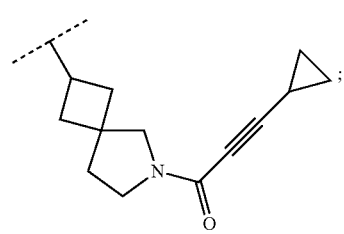

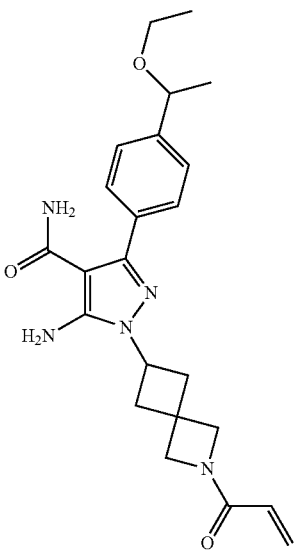

or a pharmaceutically acceptable salt thereof.

In another embodiment, the invention provides made compounds in Table I which can be made in view of the general schemes, examples and methods known in the art.

Table of compounds and Biological activity

| Example | Structure | BTK IC50 (nM) | HPLC Method | RT (min) | m/z [M + H]+ |
|---|---|---|---|---|---|
| 1 | 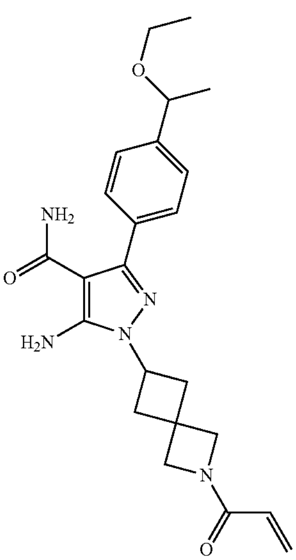 [SMILES: C=CC(=O)N1CC2(CC(n3nc(-c4ccc(C(C)OCC)cc4)c(C(N)=O)c3N)C2)C1] | 100 | A | 0.69 | 424.3 |

-continued
Table of compounds and Biological activity
| Example | Structure | BTK IC50 (nM) | HPLC Method | RT (min) | m/z [M + H]+ |
|---|---|---|---|---|---|
| 2 | 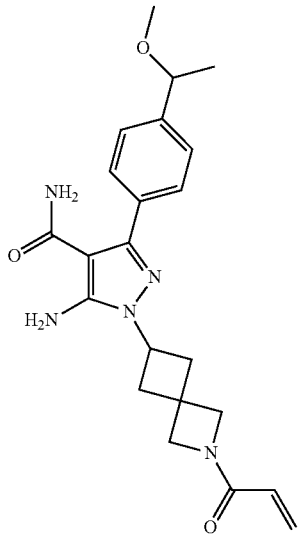 [SMILES: C=CC(=O)N1CC2(CC(n3nc(-c4ccc(C(C)OC)cc4)c(C(N)=O)c3N)C2)C1] | 200 | A | 0.62 | 410.3 |
| 3 | 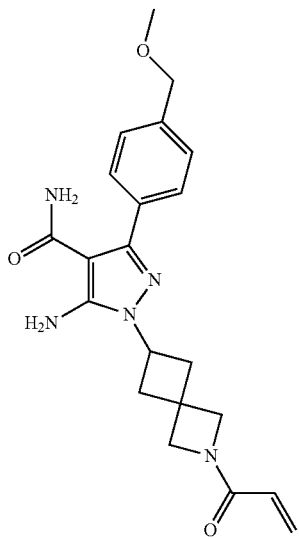 [SMILES: C=CC(=O)N1CC2(CC(n3nc(-c4ccc(COC)cc4)c(C(N)=O)c3N)C2)C1] | 94 | A | 0.57 | 396.3 |

-continued

Table of compounds and Biological activity

| Example | Structure | BTK IC50 (nM) | HPLC Method | RT (min) | m/z [M + H]+ |
| --- | --- | --- | --- | --- | --- |
| 4 | 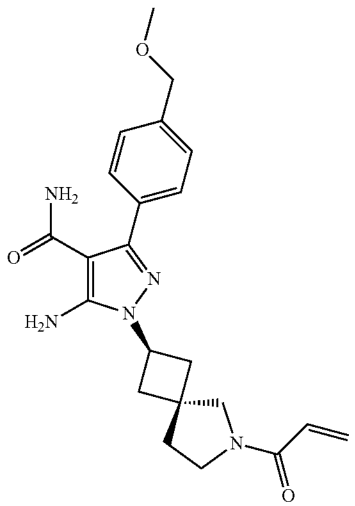 [SMILES: C=CC(=O)N1CC[C@]2(C1)C[C@H](n1nc(-c3ccc(COC)cc3)c(C(N)=O)c1N)C2] | 26 | B | 1.11 | 410.3 |
| 5 | 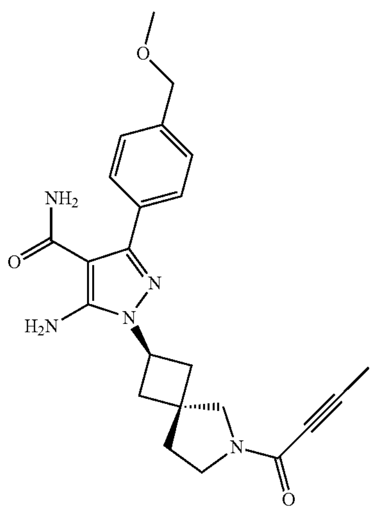 [SMILES: CC#CC(=O)N1CC[C@]2(C1)C[C@H](n1nc(-c3ccc(COC)cc3)c(C(N)=O)c1N)C2] | 2.0 | B | 1.38 | 422.2 |
| 6 | 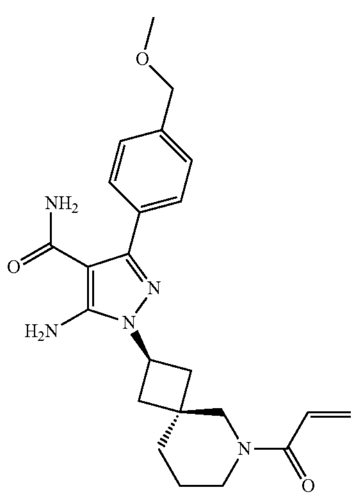 [SMILES: C=CC(=O)N1CCC[C@]2(C1)C[C@@H](n1nc(-c3ccc(COC)cc3)c(C(N)=O)c1N)C2] | 460 | B | 1.36 | 424.3 |

-continued

Table of compounds and Biological activity

| Example | Structure | BTK IC50 (nM) | HPLC Method | RT (min) | m/z [M + H]+ |
|---|---|---|---|---|---|
| 7 | 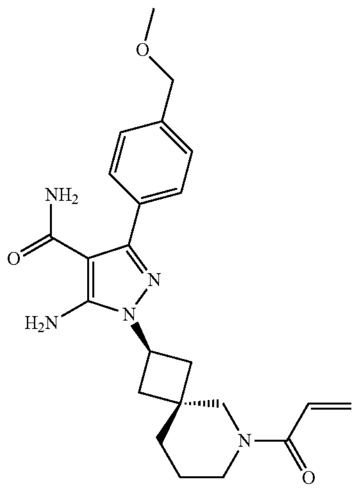 [SMILES: C=CC(=O)N1CCC[C@]2(C1)C[C@H](n1nc(-c3ccc(COC)cc3)c(C(N)=O)c1N)C2] | 450 | B | 1.50 | 424.3 |
| 8 | 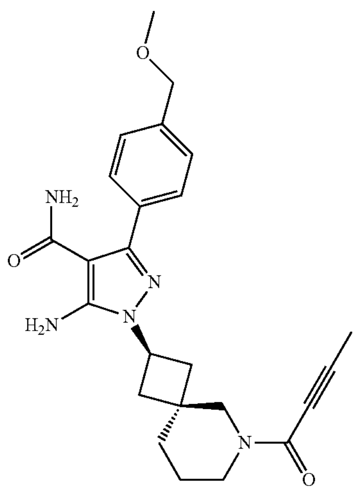 [SMILES: CC#CC(=O)N1CCC[C@]2(C1)C[C@@H](n1nc(-c3ccc(COC)cc3)c(C(N)=O)c1N)C2] | 160 | B | 1.42 | 436.3 |
| 9 | 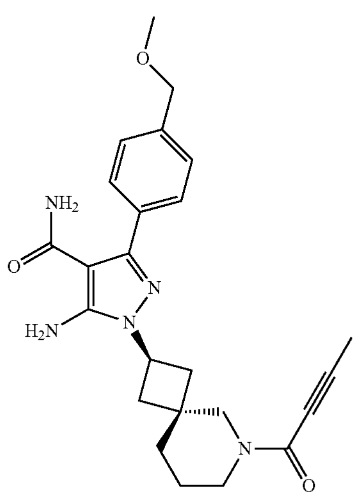 [SMILES: CC#CC(=O)N1CCC[C@]2(C1)C[C@H](n1nc(-c3ccc(COC)cc3)c(C(N)=O)c1N)C2] | 8.2 | B | 1.61 | 436.2 |

-continued

| Table of compounds and Biological activity | | | | | |
|---|---|---|---|---|---|
| Example | Structure | BTK IC50 (nM) | HPLC Method | RT (min) | m/z [M + H]+ |
| 10 | | 9.3 | B | 1.52 | 436.2 |
| 11 | | 2.2 | B | 1.58 | 436.2 |
| 12 | | 0.9 | B | 1.58 | 436.2 |

-continued
Table of compounds and Biological activity
| Example | Structure | BTK IC50 (nM) | HPLC Method | RT (min) | m/z [M + H]+ |
|---|---|---|---|---|---|
| 13 | 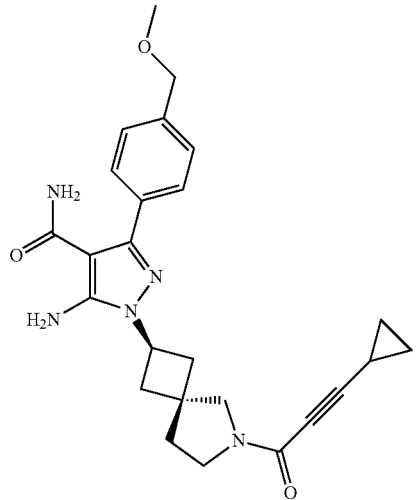 [SMILES: COCc1ccc(-c2nn([C@H]3C[C@@]4(CCN(C(=O)C#CC5CC5)C4)C3)c(N)c2C(N)=O)cc1] | 0.7 | B | 1.62 | 448.2 |
| 14 | 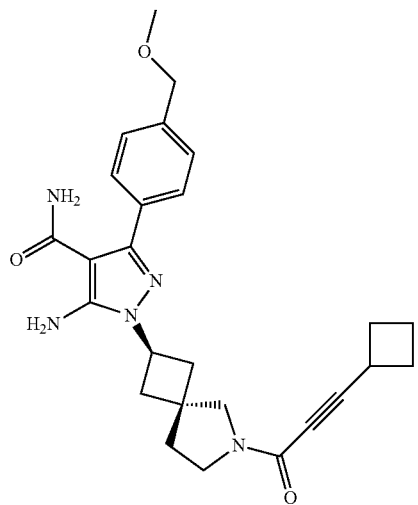 [SMILES: COCc1ccc(-c2nn([C@H]3C[C@@]4(CCN(C(=O)C#CC5CCC5)C4)C3)c(N)c2C(N)=O)cc1] | 0.6 | B | 1.9 | 462.2 |

-continued
| Example | Structure | BTK IC50 (nM) | HPLC Method | RT (min) | m/z [M + H]+ |
|---|---|---|---|---|---|
| 15 | 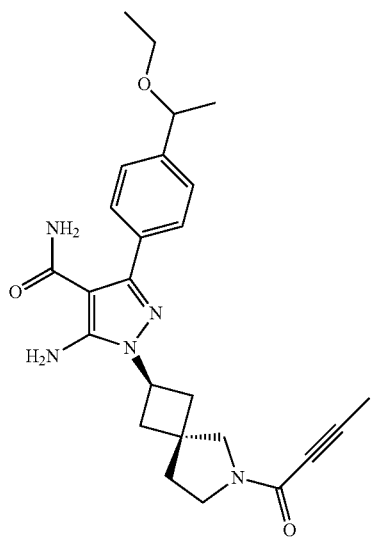 [SMILES: CC#CC(=O)N1CC[C@]2(C1)C[C@H](n1nc(-c3ccc(C(C)OCC)cc3)c(C(N)=O)c1N)C2] | 3.6 | B | 1.73 | 450.2 |
| 16 | 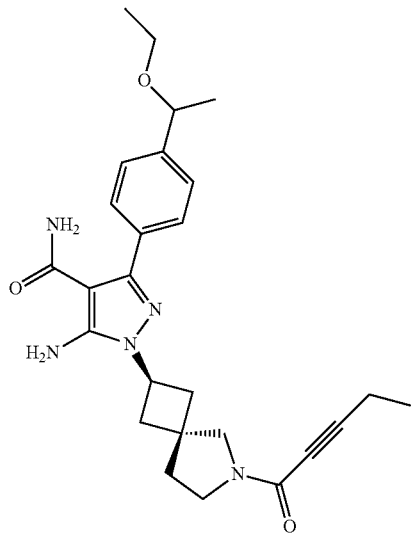 [SMILES: CCC#CC(=O)N1CC[C@]2(C1)C[C@H](n1nc(-c3ccc(C(C)OCC)cc3)c(C(N)=O)c1N)C2] | 1.8 | B | 1.96 | 464.2 |

-continued

Table of compounds and Biological activity

| Example | Structure | BTK IC50 (nM) | HPLC Method | RT (min) | m/z [M + H]+ |
|---------|-----------|---------------|-------------|----------|--------------|
| 17 | 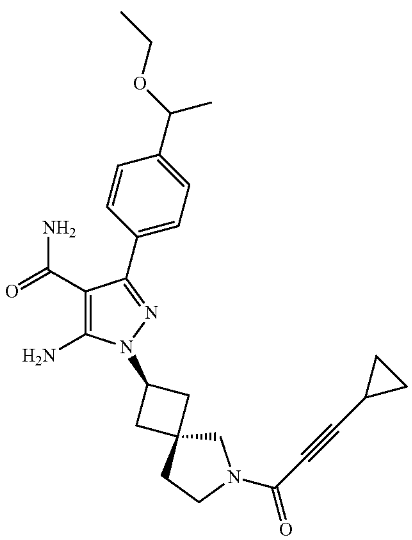 [SMILES: CCOC(C)c1ccc(-c2nn([C@H]3C[C@@]4(CCN(C(=O)C#CC5CC5)C4)C3)c(N)c2C(N)=O)cc1] | 1.2 | B | 2 | 476.2 |
| 18 | 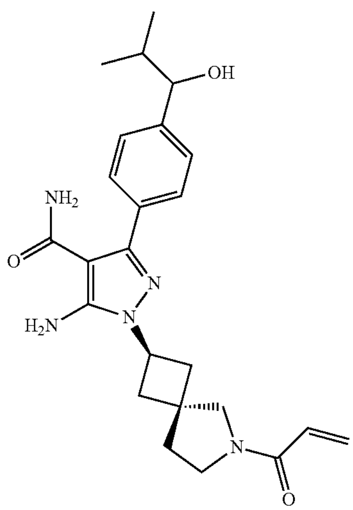 [SMILES: C=CC(=O)N1CC[C@]2(C1)C[C@H](n1nc(-c3ccc(C(O)C(C)C)cc3)c(C(N)=O)c1N)C2] | 150 | A | 0.67 | 438.4 |
| 19 | 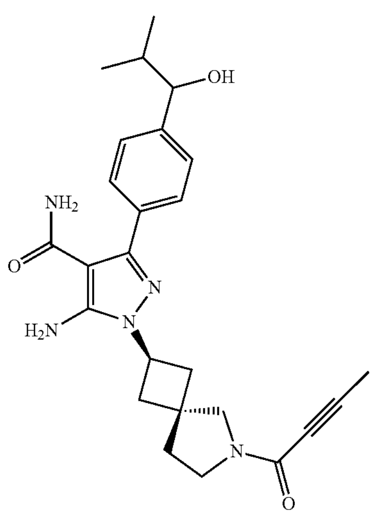 [SMILES: CC#CC(=O)N1CC[C@]2(C1)C[C@H](n1nc(-c3ccc(C(O)C(C)C)cc3)c(C(N)=O)c1N)C2] | 4.5 | A | 0.69 | 450.1 |

-continued

Table of compounds and Biological activity

| Example | Structure | BTK IC50 (nM) | HPLC Method | RT (min) | m/z [M + H]+ |
|---------|-----------|---------------|-------------|----------|--------------|
| 20 | 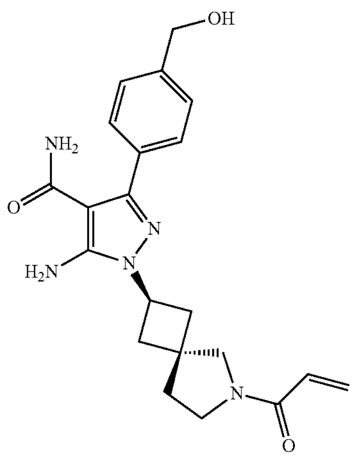 [SMILES: C=CC(=O)N1CC[C@]2(C1)C[C@H](n1nc(-c3ccc(CO)cc3)c(C(N)=O)c1N)C2] | 66 | A | 0.56 | 396.3 |
| 21 | 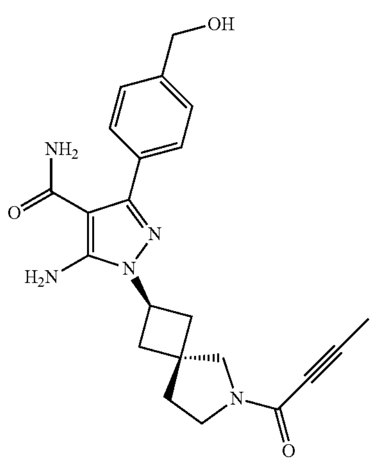 [SMILES: CC#CC(=O)N1CC[C@]2(C1)C[C@H](n1nc(-c3ccc(CO)cc3)c(C(N)=O)c1N)C2] | 2.5 | A | 0.6 | 408.2 |
| 22 | 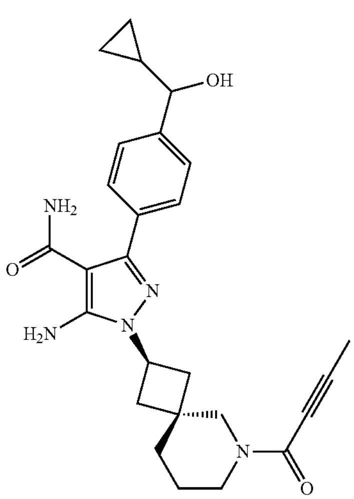 [SMILES: CC#CC(=O)N1CCC[C@]2(C1)C[C@H](n1nc(-c3ccc(C(O)C4CC4)cc3)c(C(N)=O)c1N)C2] | 59 | B | 1.39 | 462.2 |

-continued

| Table of compounds and Biological activity | | | | | |
|---|---|---|---|---|---|
| Example | Structure | BTK IC50 (nM) | HPLC Method | RT (min) | m/z [M + H]+ |
| 23 | | 68 | B | 1.27 | 450.2 |
| 24 | | 240 | A | 0.54 | 422.3 |
| 25 | | 1.4 | A | 0.57 | 422.3 |

-continued

Table of compounds and Biological activity

| Example | Structure | BTK IC50 (nM) | HPLC Method | RT (min) | m/z [M + H]+ |
|---------|-----------|---------------|-------------|----------|--------------|
| 26 | 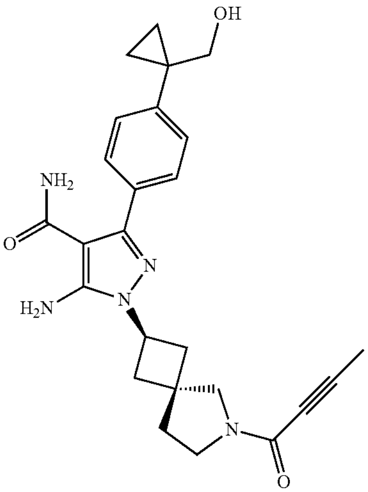 [SMILES: CC#CC(=O)N1CC[C@]2(C1)C[C@H](n1nc(-c3ccc(C4(CO)CC4)cc3)c(C(N)=O)c1N)C2] | 2.4 | A | 0.64 | 448.1 |
| 27 | | 12 | A | 0.6 | 456 | or the pharmaceutically acceptable salts thereof.

The present invention further relates to metabolites, and prodrugs of compounds of the formula (I).

The present invention further relates to a pharmaceutically acceptable salt of a compound of the formula (I) with inorganic or organic acids or bases.

In another aspect the invention relates to compounds of formula (I)—or the pharmaceutically acceptable salts thereof—as medicaments.

In another aspect the invention relates to compounds of formula (I)—or the pharmaceutically acceptable salts thereof—for use in a method for treatment of a patient.

In another aspect the invention relates to compounds of formula (I)—or the pharmaceutically acceptable salts thereof—for use in the treatment of autoimmune diseases and allergic disorders.

In another aspect the invention relates to the use of compounds of formula (I)—or the pharmaceutically acceptable salts thereof—for preparing a pharmaceutical composition for the treatment of autoimmune diseases and allergic disorders.

In another aspect the invention relates to a method for the treatment of autoimmune diseases and allergic disorders comprising administering a therapeutically effective amount of a compound of formula (I)—or one of the pharmaceutically acceptable salts thereof—to a patient.

In another aspect the invention relates to a pharmaceutical preparation containing as active substance one or more compounds of formula (I)—or the pharmaceutically acceptable salts thereof—optionally in combination with conventional excipients and/or carriers.

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x carbon atoms.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-4}$alkyl" includes for example $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), etc.

By the terms propyl, butyl, etc. without any further definition are meant saturated hydrocarbon groups with the corresponding number of carbon atoms, wherein all isomeric forms are included.

Haloalkyl is derived from the previously defined alkyl by replacing one or more hydrogen atoms of the hydrocarbon chain independently of one another by halogen atoms, which may be identical or different. If a haloalkyl is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CHFCH_2CH_3$, —$CHFCH_2CF_3$ etc.

Halogen relates to fluorine, chlorine, bromine and/or iodine atoms.

All cyclic and acyclic systems defined in this section hereinabove shall be understood to be optionally partially or fully halogenated where possible and unless otherwise indicated.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

In a representation such as for example

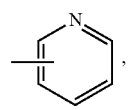

the solid line means that the ring system may be attached to the molecule via the carbon atom 1, 2 or 3, and is thus equivalent to the following representation

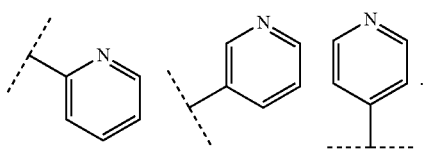

By a therapeutically effective amount for the purposes of this invention is meant a quantity of substance that is capable of obviating symptoms of illness or alleviating these symptoms, or which prolong the survival of a treated patient.

List of Abbreviations

| | |
|---|---|
| Ac | Acetyl |
| ACN | Acetonitrile |
| aq | Aqueous |
| ATP | adenosine triphosphate |
| Bn | Benzyl |
| Bu | Butyl |
| Boc | tert-butyloxycarbonyl |
| cat | Catalyst |
| conc | concentrated |
| d | day(s) |
| TLC | thin layer chromatography |
| DIEA | N,N-diisopropylethylamine |
| DMAP | 4-N,N-dimethylaminopyridine |
| DMA | N,N-dimethylacetamide |
| DME | 1,2-dimethoxyethane |
| DMF | N,N-dimethylformamide |
| DMSO | Dimethylsulphoxide |
| dppf | 1.1'-bis(diphenylphosphino)ferrocene |
| EDC | 1-Ethyl-3-(3-dimethylaminopropyl)carbodiimide |
| ESI | electron spray ionization |
| Et | Ethyl |
| $Et_2O$ | diethyl ether |
| EtOAc | ethyl acetate |
| EtOH | Ethanol |
| h | hour(s) |
| HATU | O-(7-azabenzotriazol-1-yl)-N,N,Ar,Ar-tetramethyl-uronium hexafluorophosphate |
| Hep | Heptane |
| HPLC | high performance liquid chromatography |
| i | Iso |
| LC | liquid chromatography |
| LiHMDS | lithium bis(trimethylsilyl)amide |
| sln. | Solution |
| mCPBA | 3-Chloroperoxybenzoic acid |
| Me | Methyl |
| MeOH | Methanol |
| min | Minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf (Rf) | retention factor |
| RP | reversed phase |
| RT | Retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMS | Trimethylsilyl |
| TRIS | tris(hydroxymethyl)-aminomethane |
| Ts | p-Tosyl |
| TsOH | p-toluenesulphonic acid |
| UV | Ultraviolet |

Features and advantages of the present invention will become apparent from the following detailed examples which illustrate the fundamentals of the invention by way of example without restricting its scope:

Preparation of the Compounds According to the Invention

General Synthetic Methods

Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid or 0.1% TFA and used one of the following columns:

a) Waters Sunfire OBD C18 5 µm 30×150 mm column
b) Waters XBridge OBD C18 5 µm 30×150 mm column
c) Waters ODB C8 5 µm 19×150 mm column
d) Waters Atlantis ODB C18 5 µm 19×50 mm column.
e) Waters Atlantis T3 OBD 5 µm 30×100 mm column
f) Phenomenex Gemini Axia C18 5 µm 30×100 mm column HPLC Methods:

Analytical LC/MS Analysis Method A:

Column: Waters BEH 2.1×50 mm C18 1.7 µm column

Gradient:

| Time (min) | 95%Water/5%ACN (0.05%TFA) | ACN (0.05%TFA) | Flow (ml/min) |
|---|---|---|---|
| 0 | 90 | 10 | 0.8 |
| 1.19 | 0 | 100 | 0.8 |
| 1.7 | 0 | 100 | 0.8 |

Analytical LC/MS Analysis Method B:

Column: Thermo Scientific, Aquasil C18, 50×2.1 mm, 5 µm column

Gradient:

| Time (min) | 0.1% Formic Acid in Water | 0.1% Formic Acid in CAN | Flow (ml/min) |
|---|---|---|---|
| 0 | 90 | 10 | 0.5 |
| 0.5 | 90 | 10 | 0.5 |
| 1.5 | 1 | 99 | 0.5 |
| 2.5 | 1 | 99 | 0.5 |
| 3.3 | 90 | 10 | 0.5 |
| 4.0 | 90 | 10 | 0.5 |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared as shown in Scheme Ia and Ib below.

Scheme Ia:

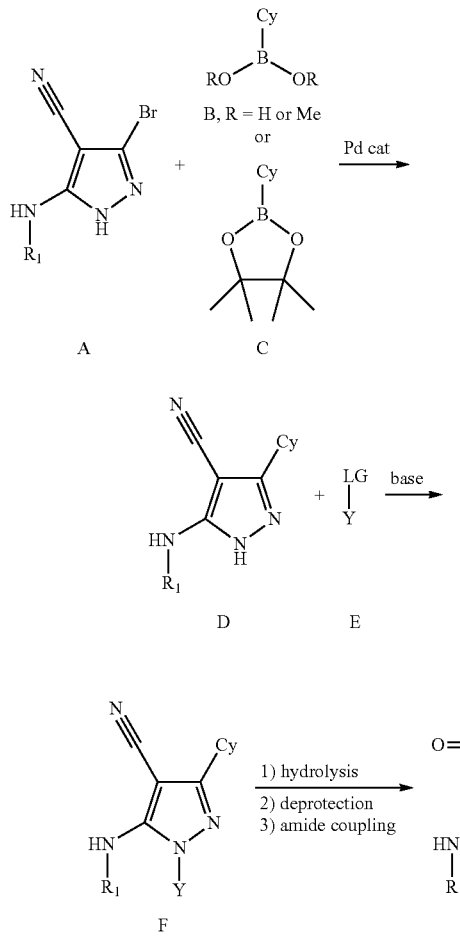

In scheme Ia, heterocycle A and either carbocycle B or C are subjected to a palladium catalysed cross-coupling reaction to generate heterocycle D. Heterocycle D is treated with a suitable base and reacted with E where LG is a leaving group to afford heterocycle F. The nitrile of heterocycle F is hydrolysed to the carboxamide followed by a deprotection and amide coupling step to afford the compound of general formula (I).

Scheme Ib:

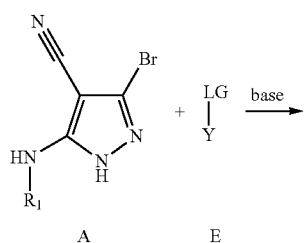

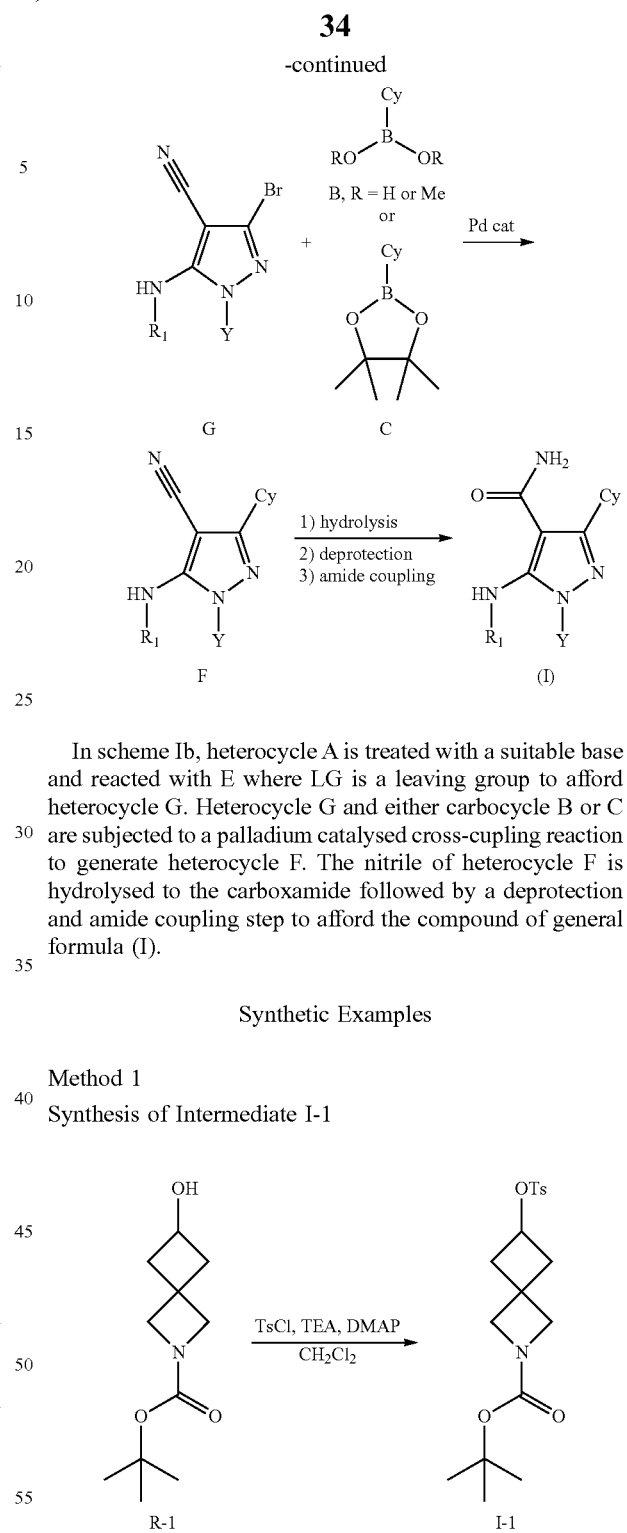

In scheme Ib, heterocycle A is treated with a suitable base and reacted with E where LG is a leaving group to afford heterocycle G. Heterocycle G and either carbocycle B or C are subjected to a palladium catalysed cross-cupling reaction to generate heterocycle F. The nitrile of heterocycle F is hydrolysed to the carboxamide followed by a deprotection and amide coupling step to afford the compound of general formula (I).

Synthetic Examples

Method 1

Synthesis of Intermediate I-1

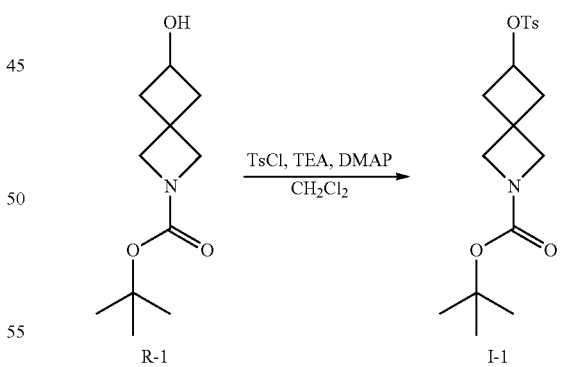

A solution of R-1 (25.0 g, 113 mmol) in CH$_2$Cl$_2$ (250 mL) is treated with TEA (31 mL, 225 mmol), TsCl (23.6 g, 124 mmol), and DMAP (2.75 g, 23 mmol). The mixture is stirred for 24 h then filtered and concentrated in vacuo. The residue is dissolved in EtOAc and washed with saturated aqueous ammonium chloride and brine. The organics are collected and volatiles are removed in vacuo. The crude residue is triturated with Et$_2$O and solid filtered and collected to afford I-1 (36.9 g, 89%) m/z 367.9 [M+].

Method 2

Synthesis of Intermediate I-2 and Separation of Diastereomers I-3 and I-4

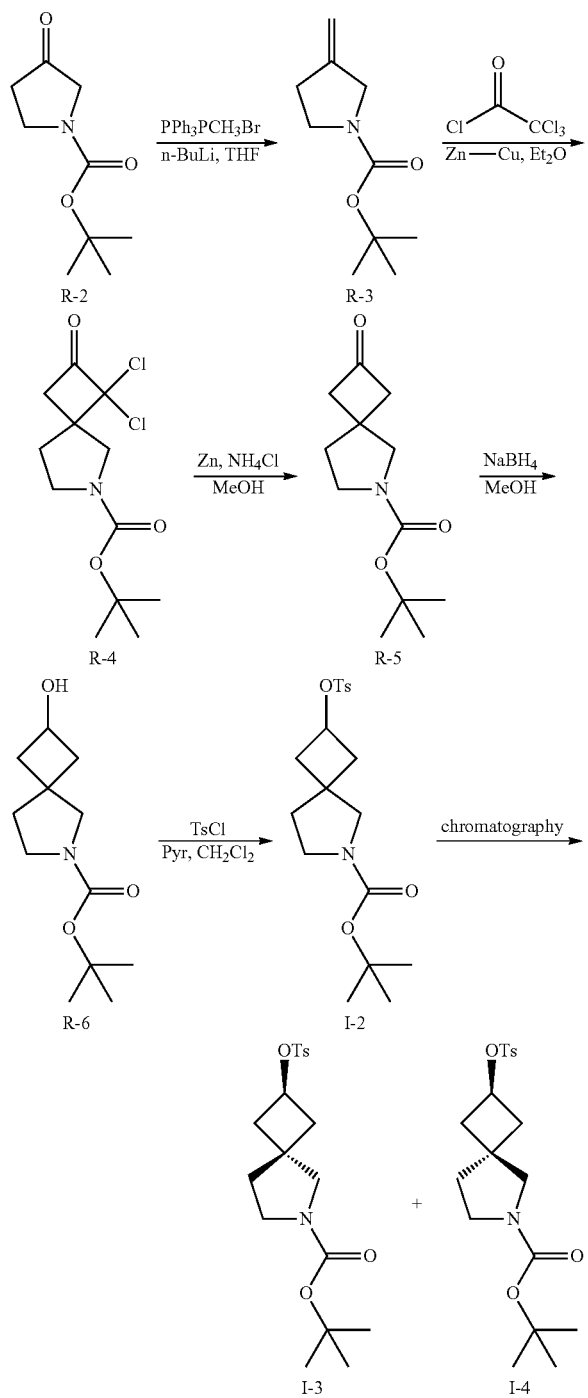

To a solution of PPh₃CH₃Br (578 g, 1.62 mol) in THF (3.5 L) is added a solution of n-BuLi (600 mL, 1.5 mol) at −78° C. under N₂. The mixture is stirred at 0° C. for 1 h then R-2 (200 g, 1.08 mol) in THF (2.0 L) is added to the reaction mixture at 0° C. The mixture is allowed to warm to ambient temperature, stirred for 1 h, then poured into H₂O and extracted with EtOAc. The organic layers are washed with brine, dried with Na₂SO₄, concentrated and purified by flash chromatography (SiO₂, Hep to 25% EtOAc in Hep) to give compound R-3 (70 g, 36%).

To a solution of R-3 (20 g, 109 mmol) in Et₂O (150 mL) is added Zn—Cu (56.2 g, 436 mmol) at 10° C. under N₂. Trichloroacetyl chloride (39.7 g, 218 mmol) in DME (150 mL) is added. The mixture is allowed to warm to ambient temperature and stirred for 2 days. The mixture is treated with aqueous NaHCO₃ and extracted with EtOAc. The organic layers are washed with brine, dried with Na₂SO₄, concentrated and purified by flash chromatography (SiO₂, Hep to 25% EtOAc in Hep) to give R-4 (11 g, 34%).

To a solution of R-4 (82.0 g, 279 mmol) and NH₄Cl (151 g, 2790 mmol) in MeOH (1000 mL) is added Zn (90.6 g, 1390 mmol). The mixture is stirred at rt for 24 h. The mixture is treated with H₂O and extracted with EtOAc. The organic layers are washed with brine, dried with Na₂SO₄, concentrated and purified by flash chromatography (SiO₂, Hep to 25% EtOAc in Hep) to afford R-5 (40 g, 64%).

To the mixture of R-5 (19 g, 84.3 mmol) in THF (200 mL) is added NaBH₄ (12.8 g, 337.2 mmol) at 0° C. and then stirred at ambient temperature for 6 h. The mixture is treated with MeOH and H₂O, then extracted with EtOAc. The organic layers are washed with brine, dried with Na₂SO₄, concentrated and purified by flash chromatography (SiO₂, Hep to 50% EtOAc in Hep) to yield R-6 (12 g, 63%).

To the mixture of R-6 (22 g, 96.8 mmol) and pyridine (23.2 g, 290.4 mmol) in CH₂Cl₂ (300 mL) is added TsCl (27.7 g, 145.2 mmol) at 0° C. and then stirred at ambient temperature overnight. The mixture is treated with H₂O and extracted with EtOAc. The organic layers are washed with brine, dried with Na₂SO₄, concentrated and purified by flash chromatography (SiO₂, Hep to 40% EtOAc in Hep) to give I-2 (26.6 g, 72%) m/z 382.2 [M+H]. I-2 is separated by flash chromatography (SiO₂, 15% THF in Hep) to give diastereomers I-3 (m/z 382.2 [M+H]) and I-4 (m/z 382.2 [M+H]).

Method 3

Synthesis of Intermediate I-5

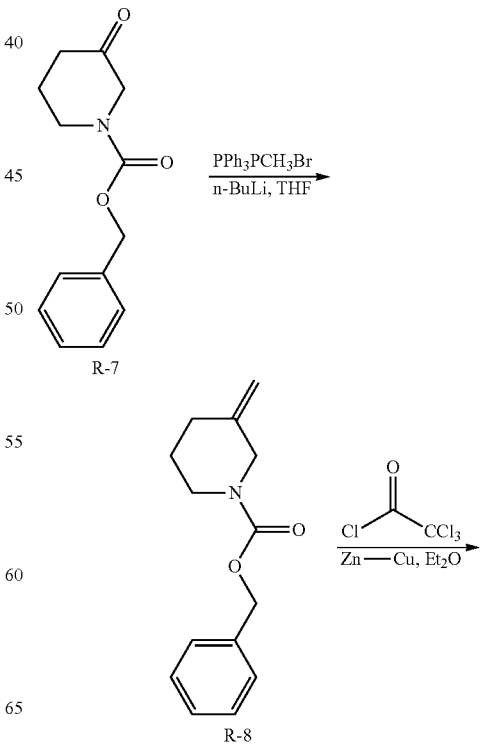

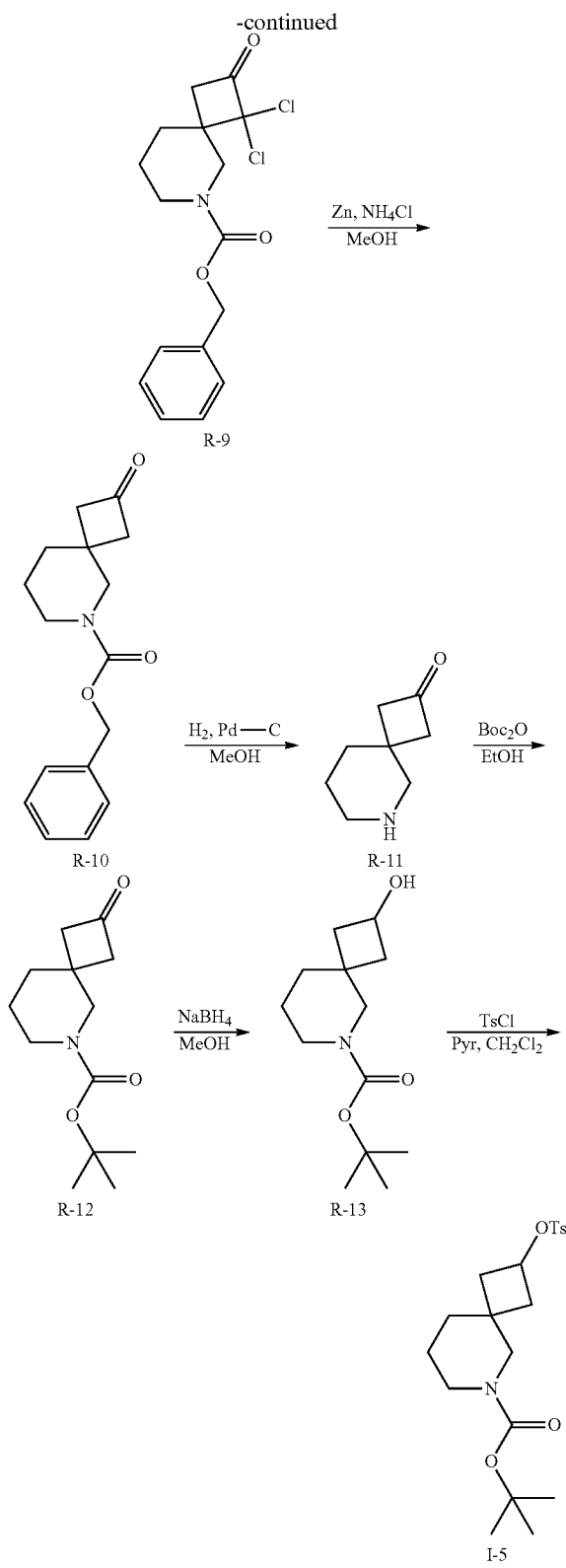

extracted with EtOAc. The organic layers are washed with brine, dried with Na₂SO₄, concentrated and purified by flash chromatography (SiO₂, Hep to 25% EtOAc in Hep) to give compound R-8 (45 g, 45%).

To a solution of R-8 (20.0 g, 86 mmol) in 1,4-dioxane (200 mL) is added Zn—Cu (33.2 g, 259 mmol) at rt under N₂. Trichloroacetyl chloride (31.4 g, 173 mmol) in 1,4-dioxane (200 mL) is added. The mixture is allowed to warm to rt and stirred for 2 days. The mixture is treated with aqueous NaHCO₃ and extracted with EtOAc. The organic layers are washed with brine, dried with Na₂SO₄, concentrated and purified by flash chromatography (SiO₂, Hep to 25% EtOAc in Hep) to give R-9 (11 g, 34%).

To a solution of R-9 (44.0 g, 129 mmol) in MeOH (400 mL) is added Zn (83.6 g, 1.29 mol) and NH₄Cl (68.8 g, 1.29 mol) dissolved in water (160 mL). The mixture is stirred at rt for 8 h then filtered. The filtrate is concentrated and purified by flash chromatography (SiO₂, Hep to 25% EtOAc in Hep) to afford R-10 (26.7 g, 76%).

A suspension of R-10 (26.7 g, 98 mmol) and 10% Pd/C (6.0 g) in MeOH (250 mL) is stirred under an atmosphere of H₂ at 50 psi at rt overnight. The mixture is filtered and concentrated to afford R-11 (12.2 g, 90%).

To a solution of R-11 (12.2 g, 88 mmol) in CH₂Cl₂ (120 mL) is added Boc anhydride (38.3 g, 175 mmol) and TEA (44.3 g, 438 mmol). The mixture is stirred at rt for 5 h then concentrated and purified by flash chromatography (SiO₂, Hep to 25% EtOAc in Hep) to give R-12 (17.4 g, 83%).

To a solution of R-12 (9.5 g, 40 mmol) in MeOH (200 mL) is added NaBH₄ (2.26 g, 60 mmol) at 0° C. portionwise and then stirred at rt for 6 h. The mixture is treated with water, then extracted with EtOAc. The organic layers are washed with brine, dried with Na₂SO₄, concentrated and purified by flash chromatography (SiO₂, Hep to 50% EtOAc in Hep) to yield R-13 (7.1 g, 74%).

To the mixture of R-13 (7.1 g, 29 mmol) and pyridine (11.8 g, 147 mmol) in CH₂Cl₂ (100 mL) is added TsCl (28.0 g, 147 mmol). The mixture is stirred at rt for 24 h then treated with H₂O, extracted with EtOAc, dried with Na₂SO₄, concentrated and purified by flash chromatography (SiO₂, Hep to 40% EtOAc in Hep) to give I-5 (10 g, 86%) m/z 396.6 [M+H].

Method 4

Synthesis of Intermediate I-6

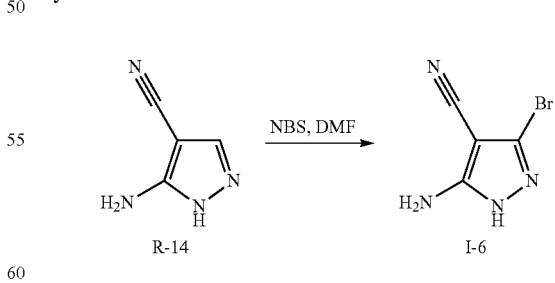

To a solution of PPh₃CH₃Br (230 g, 0.64 mol) in THF (0.8 L) is added a solution of n-BuLi (240 mL, 0.6 mol) at 0° C. under N₂. The mixture is stirred at 0° C. for 1 h then R-7 (100 g, 0.43 mol) in THF (0.8 L) is added to the reaction mixture at 0° C. The mixture is allowed to warm to ambient temperature, stirred for 1 h, then poured into H₂O and To a solution of R-14 (100 g, 0.9 mol) in DMF (1 L) is added NBS (197.5 g, 1.1 mol) and mixture is stirred for 10 h at ambient temperature. The mixture is concentrated in vacuo then dissolved in EtOAc and washed with brine (8×). The organics are collected and concentrated in vacuo to afford I-6 (50 g, 29%) m/z 187.0 [M+].

Method 5
Synthesis of Intermediate I-7

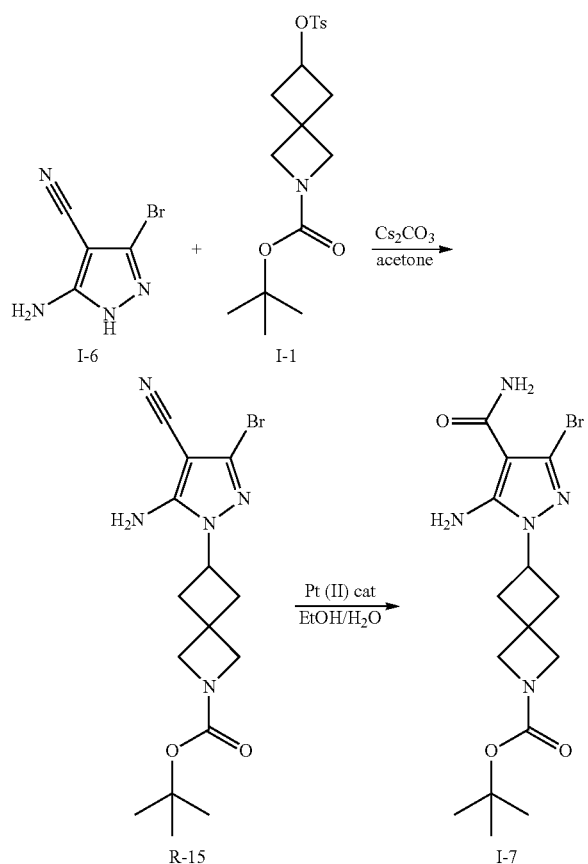

To a solution of I-6 (22 g, 118 mmol) in acetone (250 mL) is added Cs$_2$CO$_3$ (76 g, 236 mmol). The mixture is heated at 80° C. for 2 days then cooled to rt and diluted with water (200 mL), extracted with CH$_2$Cl$_2$ (2×), dried over Na$_2$SO$_4$, filtered and concentrated. The residue is purified by flash chromatography (SiO$_2$, Hep to 70% EtOAc in Hep) to give R-15 (25 g, 46%).

To a solution of R-15 (5.3 g, 13.2 mmol) in EtOH (90 mL) and water (30 mL) is added hydrido(dimethylphosphinous acid kP) [hydrogen bis(dimethylphosphinito-kP)] platinum (II) (562 mg, 1.32 mmol). The mixture is heated at 80° C. for 24 h then concentrated in vacuo. The residue is diluted with EtOAc, filtered, and concentrated in vacuo to afford I-7 (5.0 g, 95%) m/z 400.3 [M+].

Method 6
Synthesis of Intermediate I-8

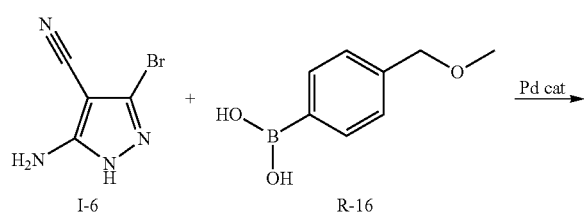

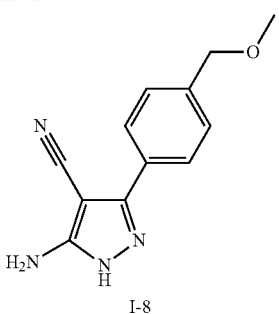

A solution of I-6 (4.00 g, 21.4 mmol), tetrakis(triphenylphosphine)palladium (0) (2.47 g, 2.14 mmol), and R-16 (3.91 g, 23.5 mmol) in 1,4-dioxane (40 mL) and 2M aqueous K$_2$CO$_3$ (40 mL) is heated in a sealed tube at 130° C. for 24 h. The mixture is cooled to rt and layers are separated. The organics are collected and concentrated to afford a residue that is purified by flash chromatography (SiO$_2$, Hep/EtOAc) to give I-8 (2.2 g, 45%) m/z 229.3 [M+H].

The following intermediates are prepared in similar fashion

| Structure | Intermediate | m/z |
|---|---|---|
| 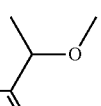 | I-9 | 243.1 [M + H] |
| 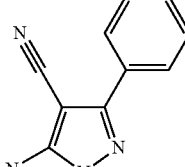 | I-10 | 243.3 [M + H] |
| 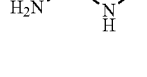 | I-11 | 257.1 [M + H] |

| Structure | Intermediate | m/z |
|---|---|---|
| 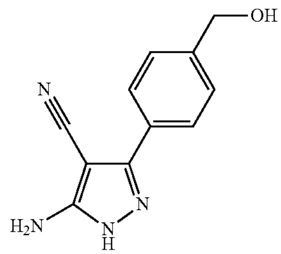 [SMILES: N#Cc1c(-c2ccc(CO)cc2)n[nH]c1N] | I-12 | 213.3 [M − H] |
| 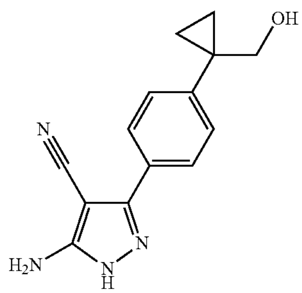 [SMILES: N#Cc1c(-c2ccc(C3(CO)CC3)cc2)n[nH]c1N] | I-13 | 255.4 [M + H] |
| 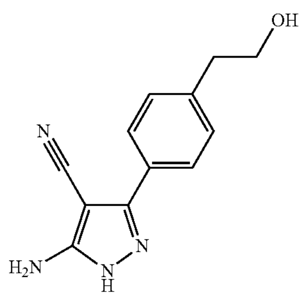 [SMILES: N#Cc1c(-c2ccc(CCO)cc2)n[nH]c1N] | I-14 | 229.1 [M + H] |
| 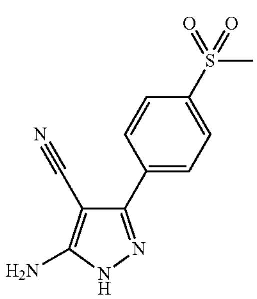 [SMILES: CS(=O)(=O)c1ccc(-c2n[nH]c(N)c2C#N)cc1] | I-15 | 263.1 [M + H] |

Method 7
Synthesis of Intermediate I-16

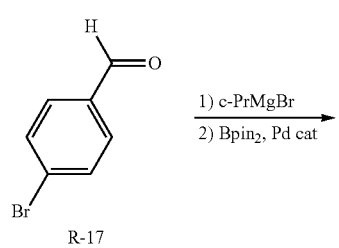

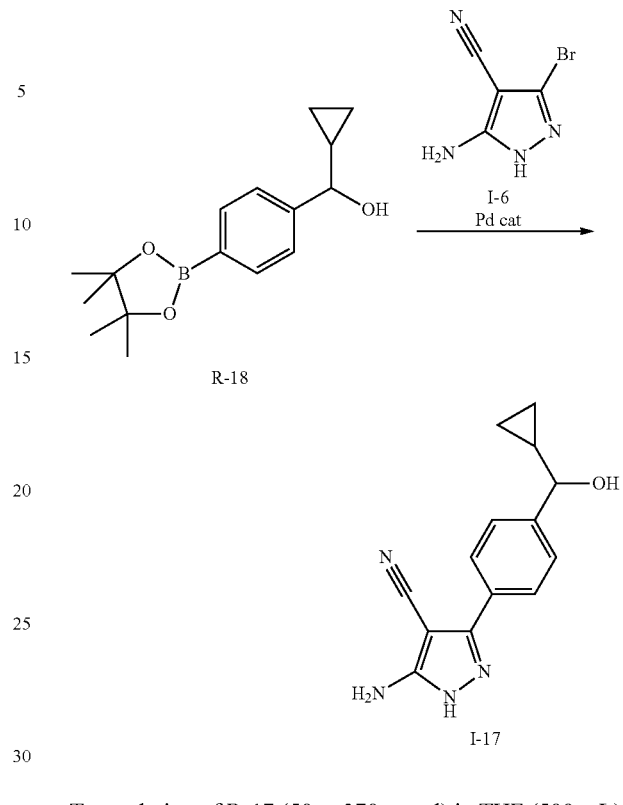

To a solution of R-17 (50 g, 270 mmol) in THF (500 mL) is added a solution of c-PrMgBr (0.5 M in THF, 810 mL, 405 mmol) at 0° C. then allowed to warm to rt. The mixture is stirred an additional 6 h at 50° C. then cooled to rt, treated with water, extracted with EtOAc, dried over Na$_2$SO$_4$, filtered and concentrated. The residue is purified by flash chromatography (SiO$_2$, Hep/EtOAc) to give R-18 (15 g, 24%).

To a solution of R-18 (17.4 g, 77 mmol), KOAc (15 g, 153 mmol), and Bpin$_2$ (29 g, 115 mmol) in 1,4-dioxane (225 mL) is added Pd(dppf)Cl$_2$ (11 g, 15 mmol). The mixture is heated at 85° C. for 12 h then cooled to rt, treated with water, extracted with EtOAc, dried over Na$_2$SO$_4$, filtered and concentrated. The residue is purified by flash chromatography (SiO$_2$, Hep/EtOAc) to give I-17 (5.2 g, 25%) m/z 257 [M−OH].

The following intermediate is prepared in similar fashion

| Structure | Intermediate | m/z |
|---|---|---|
| 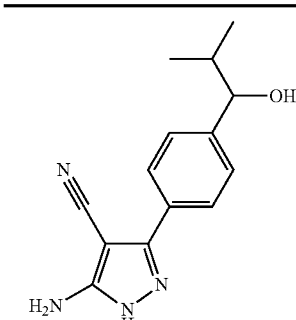 | I-16 | 257.1 [M + H] |

Method 8
Synthesis of Example 1

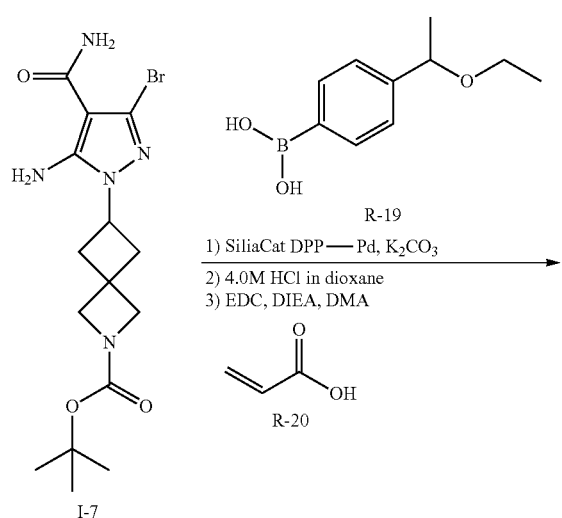

Example 1

To a solution of I-7 (60 mg, 0.15 mmol) in DME (2 mL) is added R-16 (44 mg, 0.23 mmol). To this solution is added aqueous 2 M $K_2CO_3$ (375 µL) and SiliaCat DPP-Pd (60 mg). The mixture is heated at 120° C. for 16 h then cooled to rt, partitioned between DCE and water, organics collected and concentrated in vacuo. The residue is dissolved in DCE (2 mL) and TFA (1 mL) is added. The mixture is stirred for 16 h then volatiles are removed in vacuo. To this residue is added a solution of acrylic acid (13 mg, 0.18 mmol), EDCI (43 mg, 0.23 mmol), and DIEA (58 mg, 0.45 mmol) in DMA (0.8 mL). The reaction mixture is stirred for 16 h then volatiles were removed in vacuo to afford a residue that is purified by RHPLC to afford example 1 (3.2 mg, 5%).

The following compounds were prepared in a similar manner:

Examples 2-3, 24

Method 9
Synthesis of Example 5

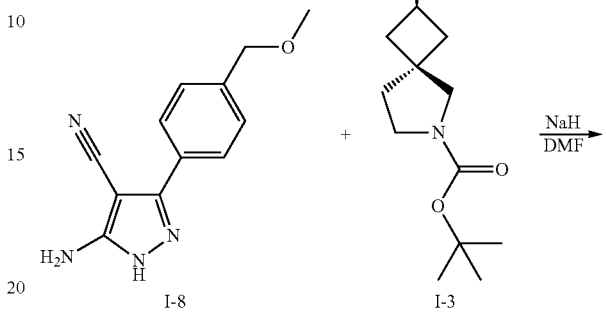

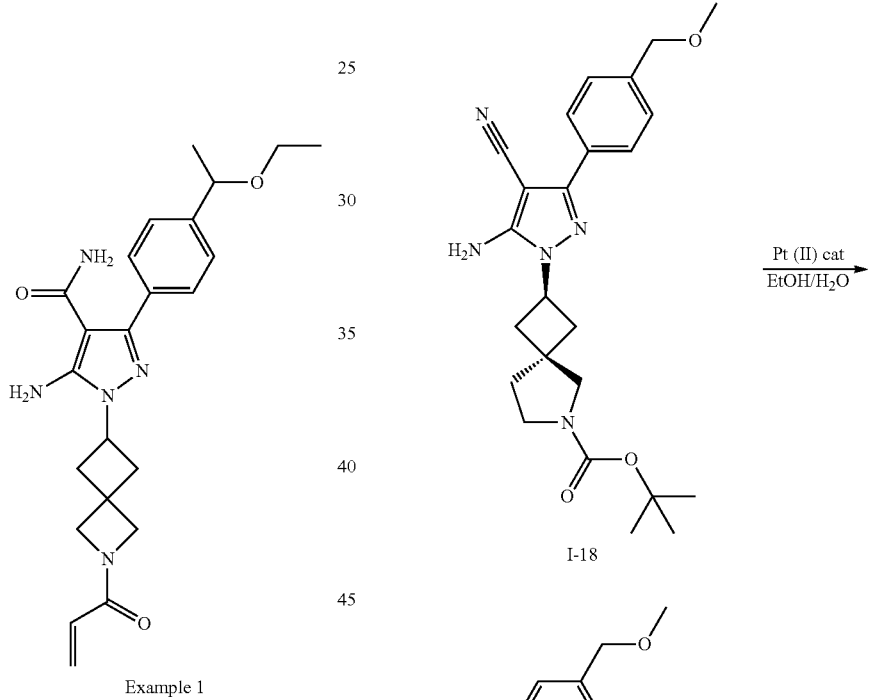

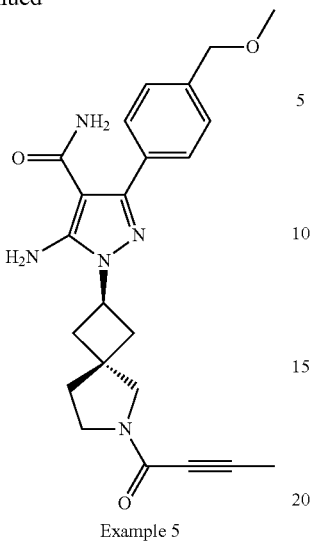

Example 5

A solution of I-8 (1.00 g, 4.38 mmol) in DMF (10 mL) is treated with NaH (60% dispersion in mineral oil, 200 mg, 5.23 mmol). The solution is stirred for 5 min then treated with I-4 (1.84 g, 4.82 mmol) and heated at 80° C. for 18 h. The mixture is cooled to rt then treated with water, extracted with EtOAc, dried over Na₂SO₄, filtered and concentrated. The residue is purified by flash chromatography (SiO₂, Hep to 70% EtOAc in Hep) to afford I-18 (900 mg, 47%) m/z 438.2 [M+H].

To a solution of I-18 (600 mg, 1.37 mmol) in EtOH (5 mL) and water (2 mL) is added hydrido(dimethylphosphinous acid kP) [hydrogen bis(dimethylphosphinito-kP)] platinum (II) (11 mg, 0.026 mmol). The mixture is heated at 80° C. for 2 days then concentrated. The residue is dissolved in CH₂Cl₂ then filtered and concentrated to afford I-19 (500 mg, 80%) m/z 456.2 [M+H].

To a solution of I-19 (1200 mg, 2.63 mmol) in CH₂Cl₂ (5 mL) is added a 4.0M solution of HCl in 1,4-dioxane (3 mL). The solution is stirred for 1 h then concentrated in vacuo. The crude residue is dissolved in DMF (5 mL) and treated with DIEA (1.0 mL, 5.9 mmol). To this solution is added a solution of R-21 (182 mg, 2.17 mmol) and HATU (1.54 g, 2.95 mmol) in DMF (5 mL). The mixture is stirred for 30 min then concentrated and purified by flash chromatography (SiO₂, CH₂Cl₂ to 5% MeOH in CH₂Cl₂) to afford Example 5.

The following compounds are prepared in similar fashion

| Example | Intermediate in Step 1 | Reagent in Step 2 |
|---|---|---|
| 4 | I-8 | R-20 |
| 10 | I-9 | R-21 |
| 11 | I-10 | R-21 |
| 12 | I-8 | R-22 |
| 13 | I-8 | R-23 |
| 14 | I-8 | R-24 |
| 15 | I-11 | R-21 |
| 16 | I-11 | R-22 |
| 17 | I-11 | R-23 |
| 18 | I-16 | R-20 |
| 19 | I-16 | R-21 |

-continued

| Example | Intermediate in Step 1 | Reagent in Step 2 |
|---|---|---|
| 20 | I-12 | R-20 |
| 21 | I-12 | R-21 |
| 25 | I-14 | R-21 |
| 26 | I-13 | R-21 |
| 27 | I-15 | R-21 |

Method 10
Synthesis of Intermediates I-20 and I-21

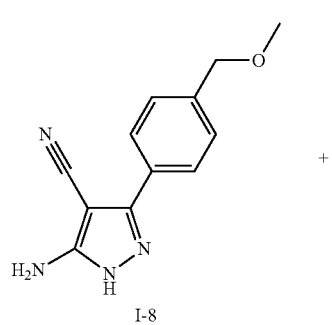

+

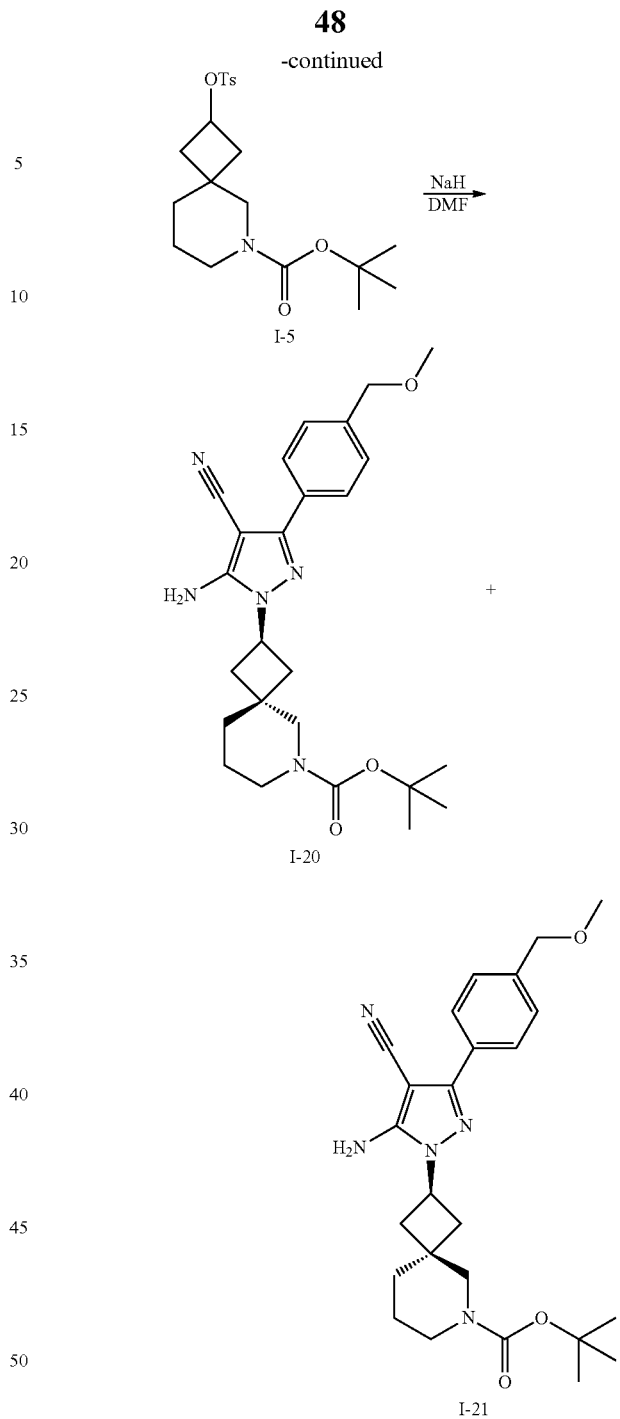

A solution of I-8 (300 mg, 1.31 mmol) in DMF (10 mL) is treated with NaH (60% dispersion in mineral oil, 60 mg, 1.58 mmol). The solution is stirred for 5 min then treated with I-5 (1.84 g, 4.82 mmol) and heated at 70° C. for 18 h. The mixture is cooled to rt then treated with water, extracted with EtOAc, dried over Na$_2$SO$_4$, filtered and concentrated. The residue is purified by flash chromatography (SiO$_2$, Hep to 70% EtOAc in Hep) to afford I-20 (150 mg, 25%) (HPLC method B; RT=2.97 min, m/z 452.3 [M+H]) and I-21 (120 mg, 20%) (HPLC method B; RT=2.71 min, m/z 452.2 [M+H]).

The following intermediates are prepared in similar fashion
| Structure | Intermediate | HPLC method | RT (min) | m/z [M + H] |
|---|---|---|---|---|
| 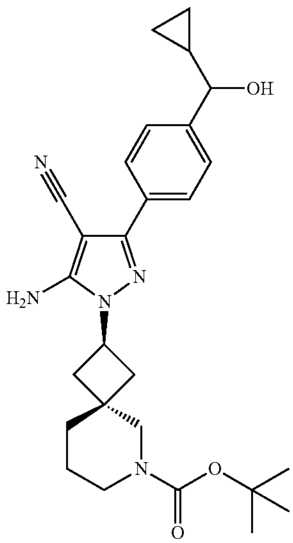 [SMILES: CC(C)(C)OC(=O)N1CCC[C@]2(C1)C[C@H](n1nc(-c3ccc(C(O)C4CC4)cc3)c(C#N)c1N)C2] | I-22 | A | 1.15 | 478.4 |
| 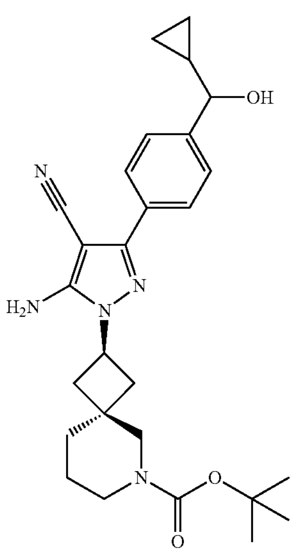 [SMILES: CC(C)(C)OC(=O)N1CCC[C@]2(C1)C[C@@H](n1nc(-c3ccc(C(O)C4CC4)cc3)c(C#N)c1N)C2] | I-23 | A | 1.07 | 478.3 |
Method 11
Synthesis of Example 9
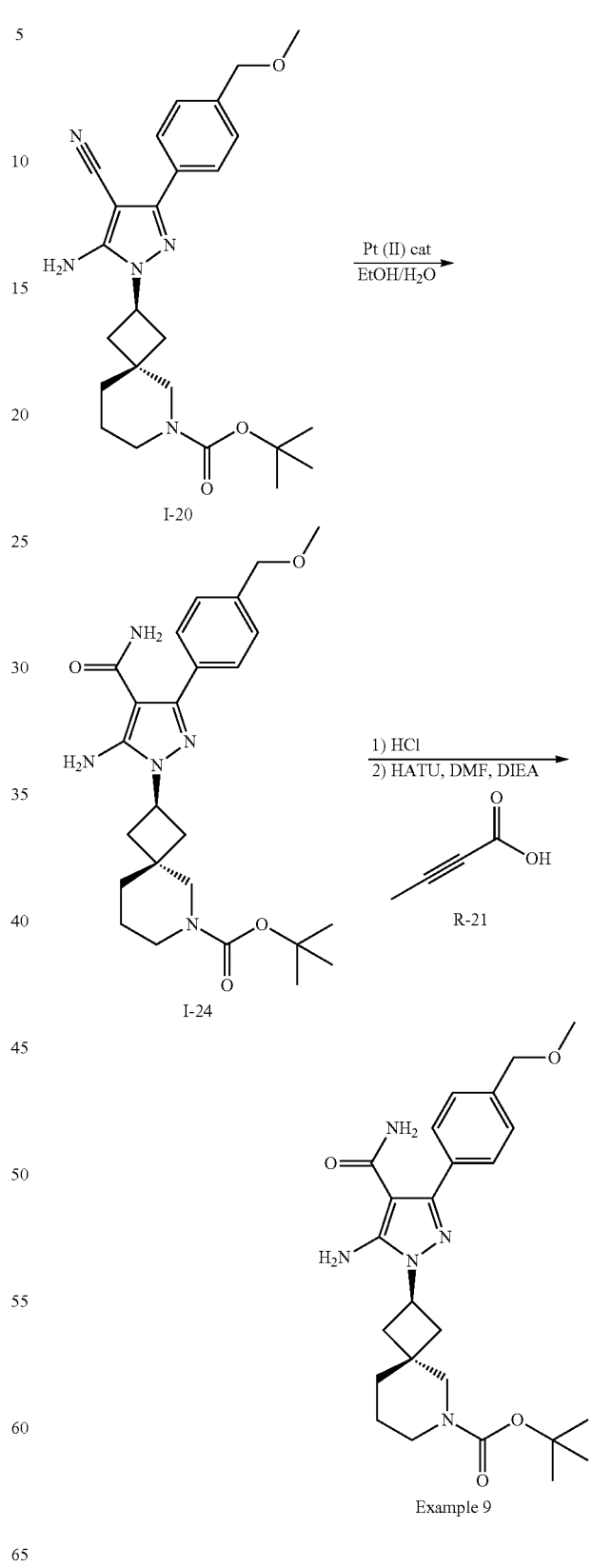
To a solution of I-20 (350 mg, 0.78 mmol) in EtOH (5 mL) and water (2 mL) is added hydrido(dimethylphosphinous acid kP) [hydrogen bis(dimethylphosphinito-kP)] platinum (II) (11 mg, 0.026 mmol). The mixture is heated at 80° C. for 2 days then concentrated. The residue is dissolved in $CH_2Cl_2$ then filtered and concentrated to afford I-24 (350 mg, 96%) m/z 470.3 [M+H].

To a solution of I-24 (140 mg, 0.27 mmol) in $CH_2Cl_2$ (4 mL) is added a 4.0M solution of HCl in 1,4-dioxane (1 mL). The solution is stirred for 1 h then concentrated in vacuo. The crude residue is dissolved in DMF (1 mL) and treated with DIEA (0.14 mL, 0.81 mmol). To this solution is added a solution of R-21 (25 mg, 0.30 mmol) and HATU (211 mg, 0.41 mmol) in DMF (1 mL). The mixture is stirred for 30 min then concentrated and purified by flash chromatography ($SiO_2$, $CH_2Cl_2$ to 5% MeOH in $CH_2Cl_2$) to afford Example 9.

The following compounds are prepared in similar fashion

| Example | Intermediate in Step 1 | Reagent in Step 1 |
|---|---|---|
| 6 | I-21 | R-20 (acrylic acid) |
| 7 | I-20 | R-20 (acrylic acid) |
| 8 | I-21 | R-21 (2-butynoic acid) |
| 22 | I-22 | R-21 (2-butynoic acid) |
| 23 | I-23 | R-20 (acrylic acid) |

Description of Biological Properties

BTK Assay

An HTRF assay (Cisbio KinEASE-TK cat #62TK0PEC) was performed to quantitate the ability of test compounds to inhibit BTK mediated phosphorylation of substrate. Assays were assembled in 384 well plates where 6 nM of full-length human His-tagged BTK (Life Technologies cat # PV3587) and test compound at varying concentrations were preincubated for 15 minutes at 28° C. Then, 1 uM of TK substrate-biotin and 30 uM ATP were added and incubated for an additional 30 minutes at 28° C. Phosphorylation was detected by adding 62.5 nM Streptavidin-XL665 and TK-Antibody Cryptate diluted 1:100 in HTRF detection buffer (Cisbio cat #62SDBRDF) and incubated for 60 minutes at RT. The plate was read on an Envision plate reader and the fluorescence is measured at 620 nm (cryptate) and 665 nm (XL665). A ratio is calculated (665/620) and converted to POC relative to control and blank wells.

Assay Buffer:

50 mM HEPES (Invitrogen #15630), 0.01% Brij-35 (sigma #B4184), 10 mM $MgCl_2$ (Sigma M1028), 1 mM EGTA (Ambion AM9262) and 100 uM sodium orthovanedate (Sigma S6508), 1 mM DTT (Sigma D5545) and 10 nM supplement enzyme buffer (Cisbio cat#61SEBALB).

Preferred compounds for the treatment of autoimmune disorders exhibit selective inhibition of BTK over other kinases such as EGFR. The compounds described herein show a range of selectivities against EGFR as measured in cellular assays (BTK activity measured by IL-6 production in primary $CD19^+$ cells; EGFR activity measured by EGFR phosphorylation in A431 cells). See Table II.

TABLE II

| Example | B-cell IL-6 $IC_{50}$ (nM) | A431 p-EGFR $IC_{50}$ (nM) |
|---|---|---|
| 5 | 2.4 | 6100 |
| 19 | 5.1 | 3000 |
| 9 | 6.3 | >10000 |
| 25 | 7.0 | >10000 |
| 27 | 93 | >10000 |

Inhibition of IL-6 Production in B Cells Co-Stimulated with ODN 2006 and Anti-hIgD Primary CD19+ B cells (AllCells # PB010F) are thawed and plated in RPMI containing 10% HI FBS in a 384-well tissue cultured plate at 20,000 cells/well. The cells are treated with test compound (0.5% DMSO final concentration) and incubated for 1 hour at 37° C., 5% CO2. Cells are then stimulated with 5 ug/mL Goat F(ab')2 anti-human IgD (SouthernBiotech #2032) and 2 uM ODN 2006 (InvivoGen # tlrl-2006) and incubated for 18-24 hours at 37° C., 5% $CO_2$. IL-6 in the supernatant is measured using Meso Scale Discovery kit # K211AKB-6.

Inhibition of EGFR Autophosphorylation in A431 Human Epithelial Cells Stimulated with Epithelial Growth Factor A431 cells (ATCC # CRL-1555 FZ) are thawed and plated in DMEM containing 10% FBS in a 384-well tissue culture treated plate at 15,000 cells/well. After incubating for 24 hours at 37° C., 5% $CO_2$, the cells are treated with test compound (1% DMSO final concentration) and incubated for 16 hours at 37° C., 5% $CO_2$. EGF (Millipore, 01-107) is added at a final concentration of 60 ng/mL and incubated for 10 minutes. The medium is removed, the cells are lysed, and phospho EGFR is measured (Meso Scale Diagnostics, N31CB-1).

Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good inhibitory effect upon BTK.

Such diseases include for example: rheumatoid arthritis, systemic lupus erythromatosis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis.

The compounds of formula (I) may be used on their own or in combination with other active substances according to the invention, optionally also in combination with other pharmacologically active substances.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

All patent and non-patent documents or literature cited in this application are herein incorporated by reference in their entirety.

The invention claimed is:
1. A compound of the formula (I)

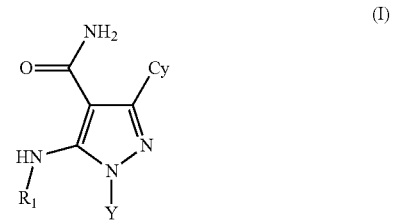

wherein
$R_1$ is H, $C_{1-4}$ alkyl;
Cy is chosen from

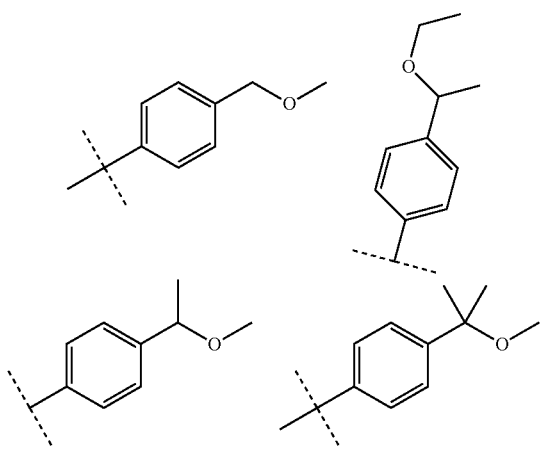

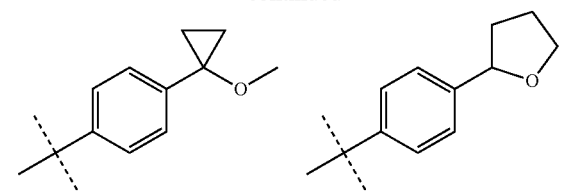
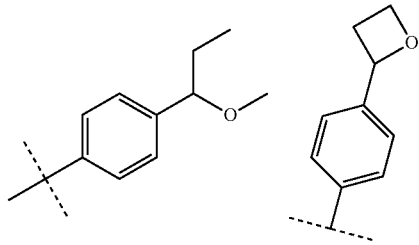
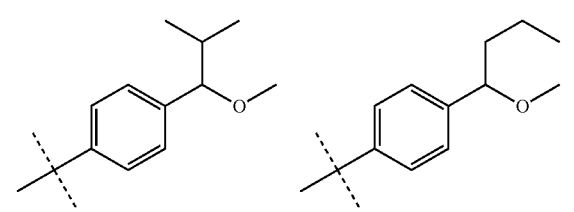
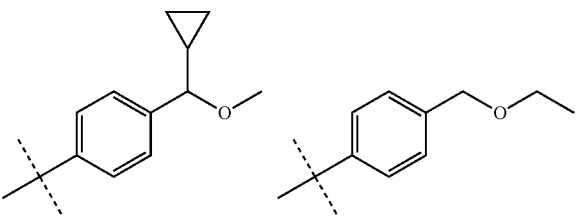
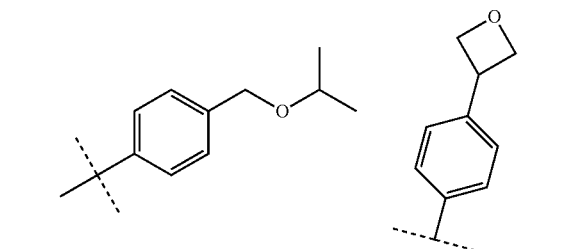
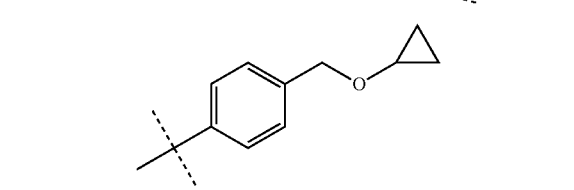
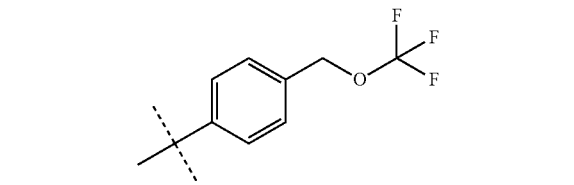
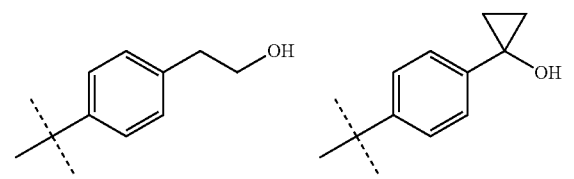
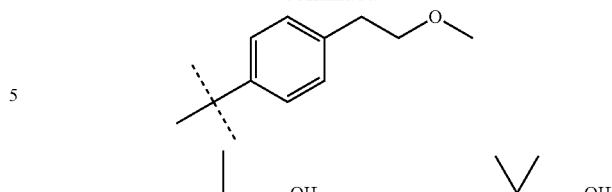
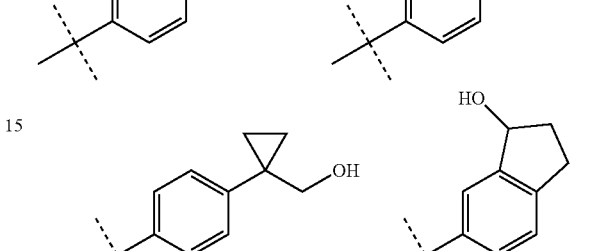
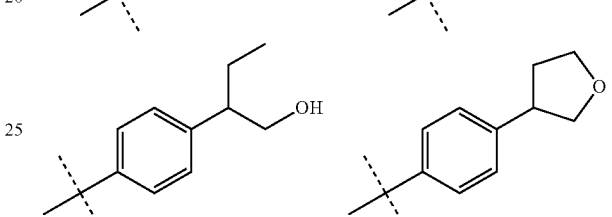
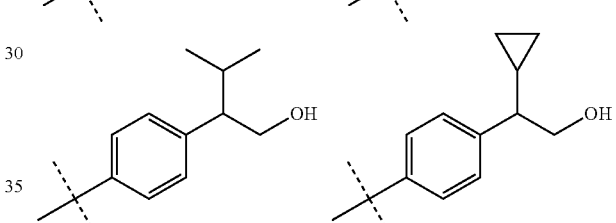
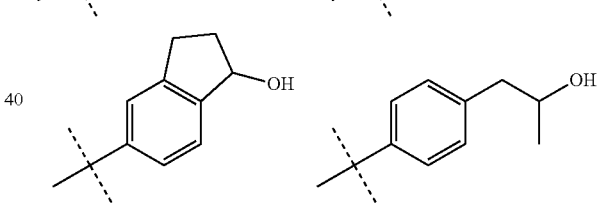
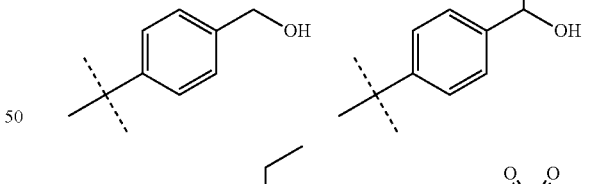
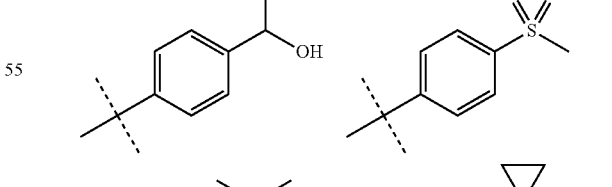
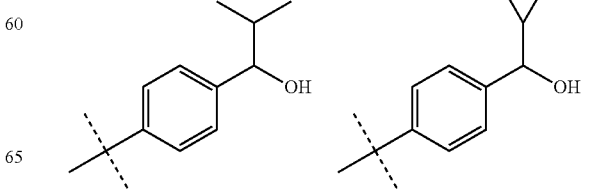

-continued

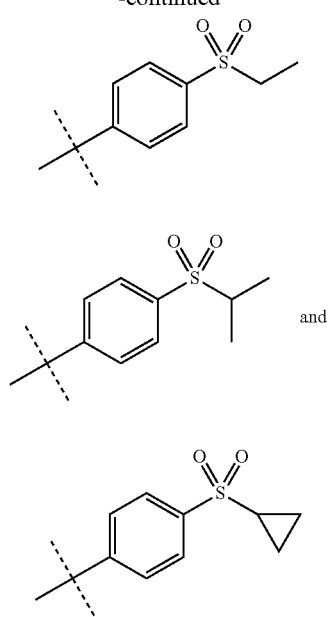

wherein each phenyl or attached substituent thereof can be optionally substituted by halogen, —CN, haloalkyl, methyl, methoxy, hydroxyl;

Y is a linker chosen from;

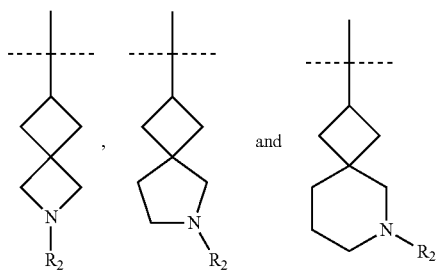

$R_2$ is chosen from

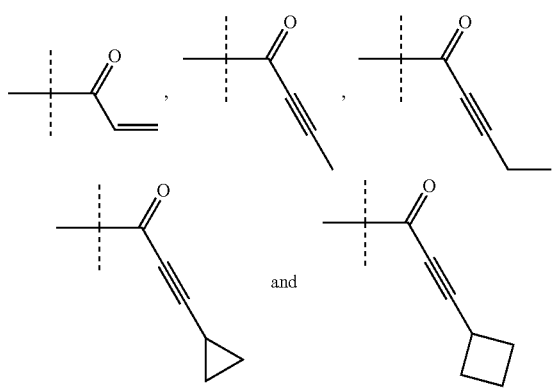

or a pharmaceutically acceptable salt thereof.

2. The compound according to claim 1 and wherein the combination of Y and R2 is chosen from:

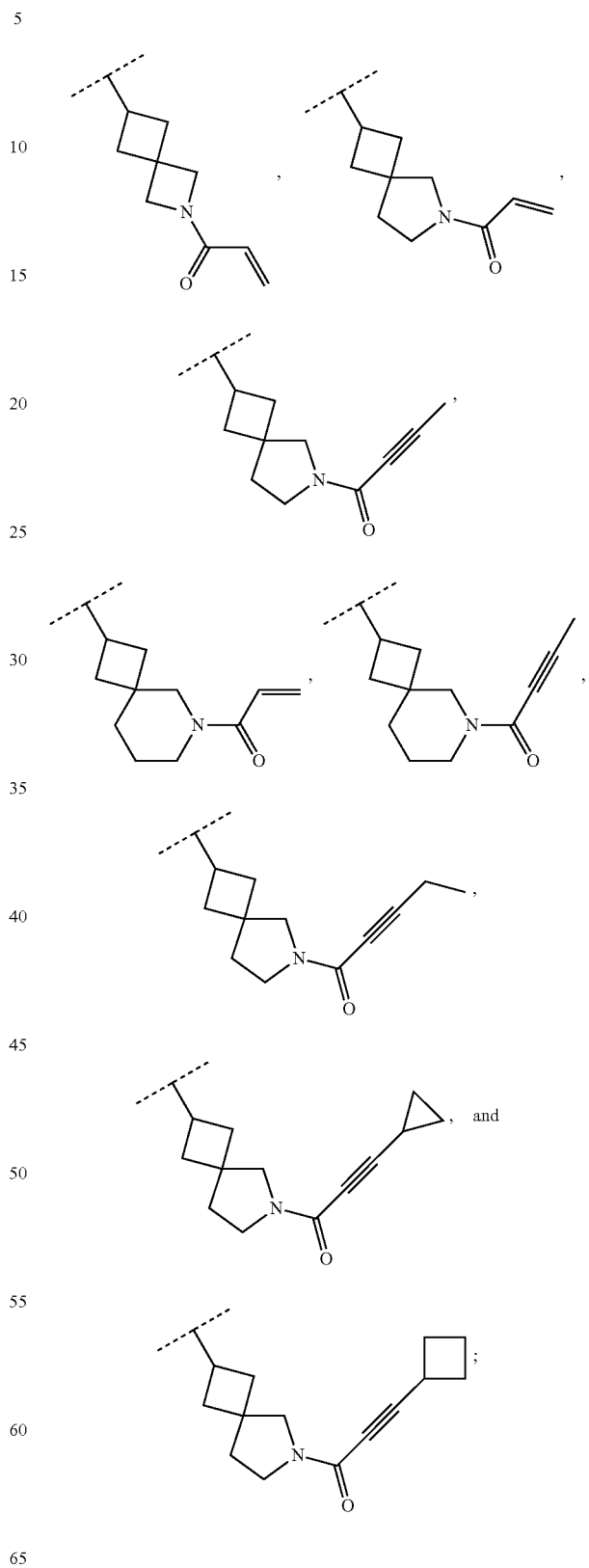

or a pharmaceutically acceptable salt thereof.

3. The compound according to claim 2 and wherein Cy is chosen from
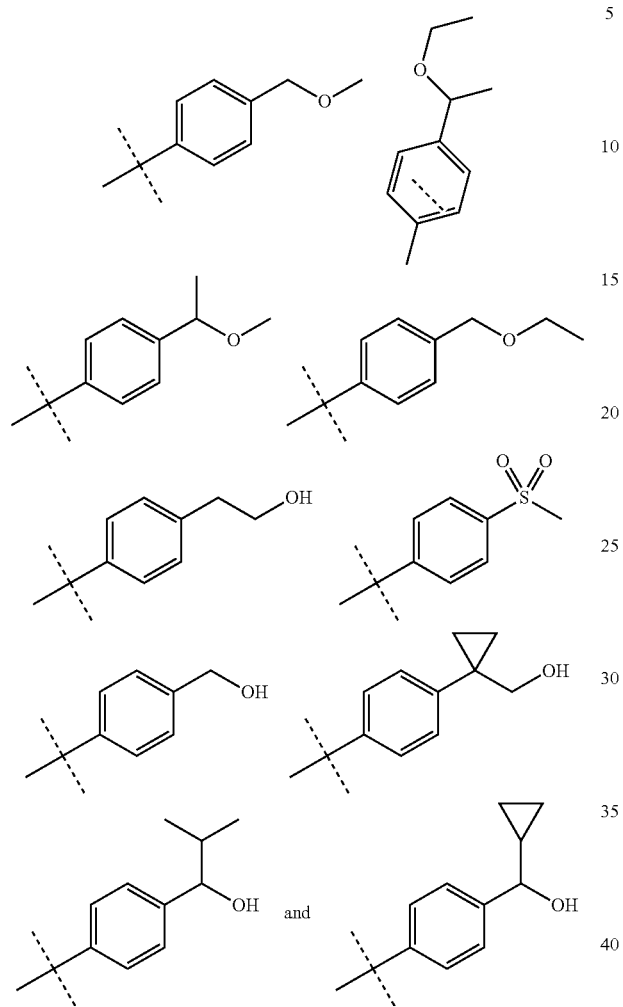
or a pharmaceutically acceptable salt thereof.
4. The compound according to claim 3 and wherein the combination of Y and R2 is chosen from:
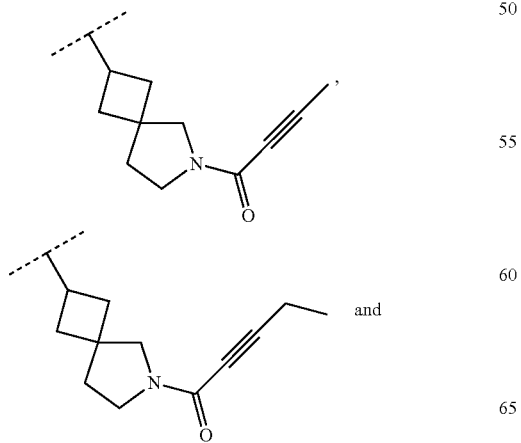
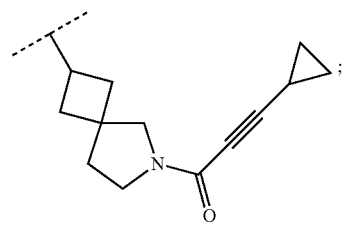
or a pharmaceutically acceptable salt thereof.
5. A compound chosen from
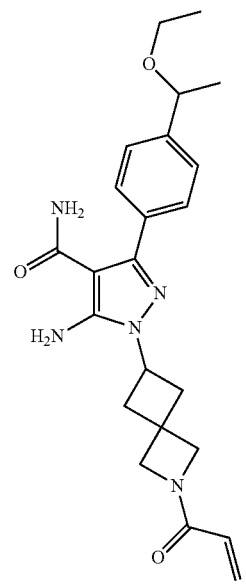
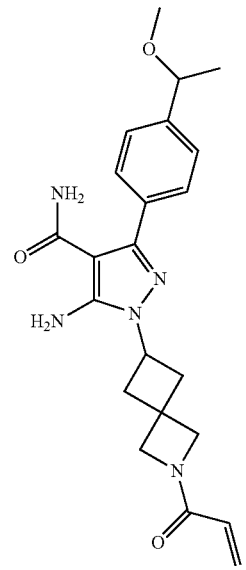

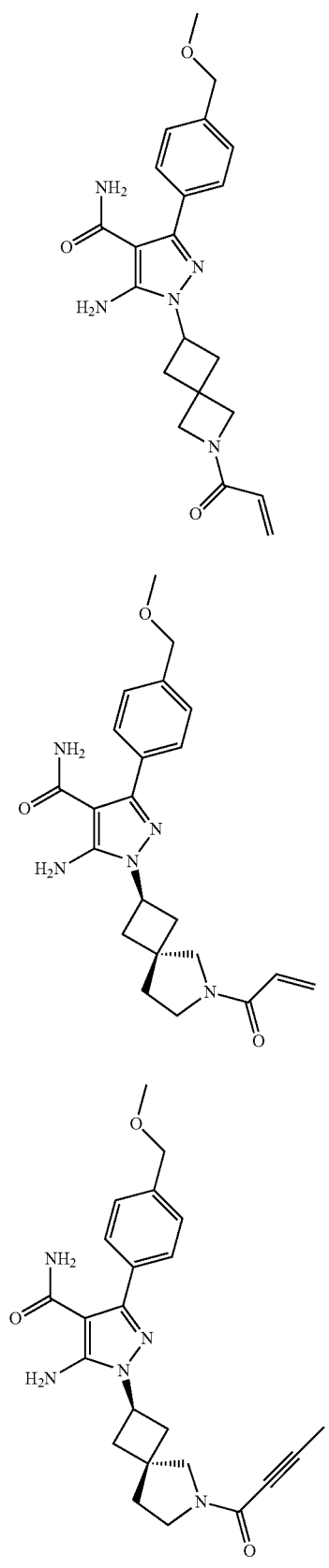
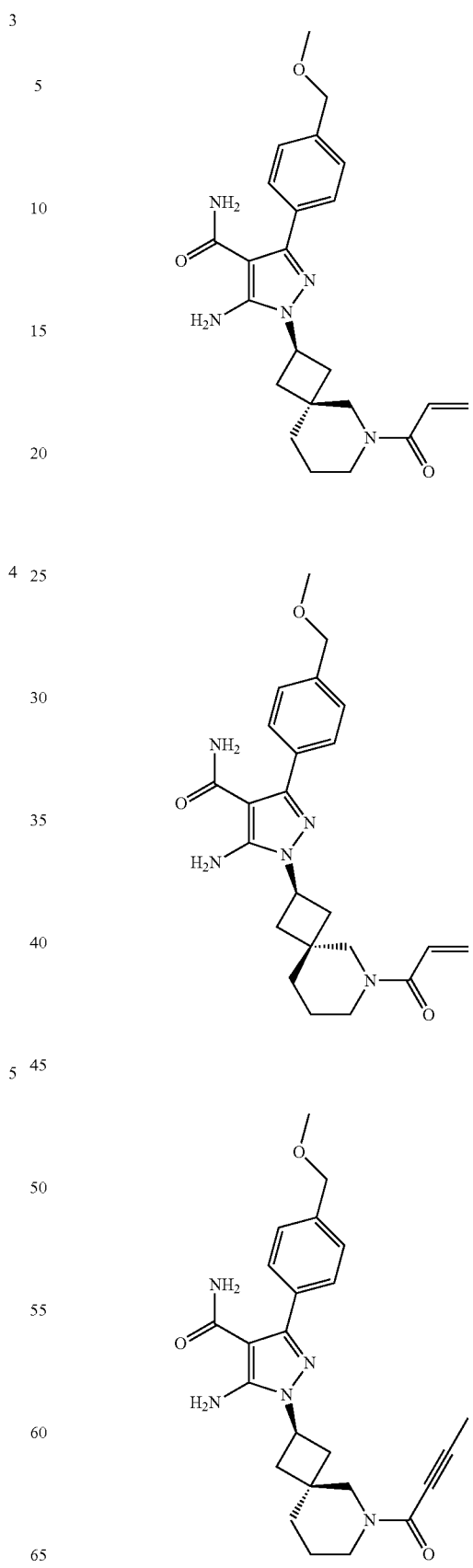

63
-continued
9
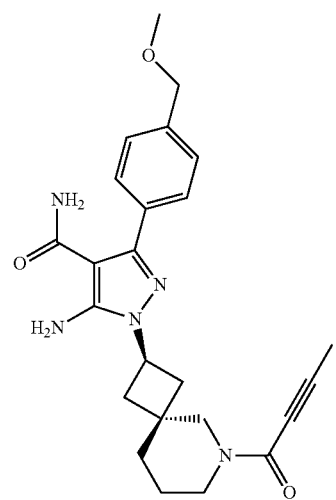
10
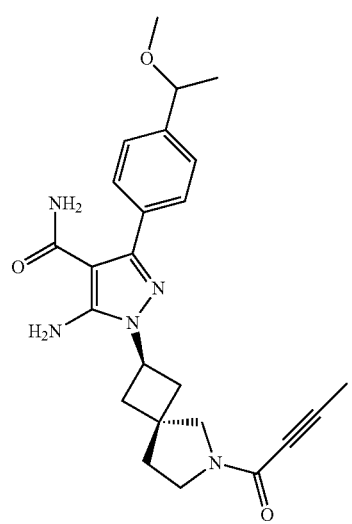
11
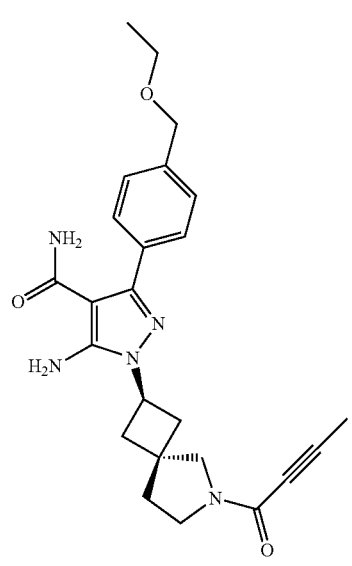
64
-continued
12
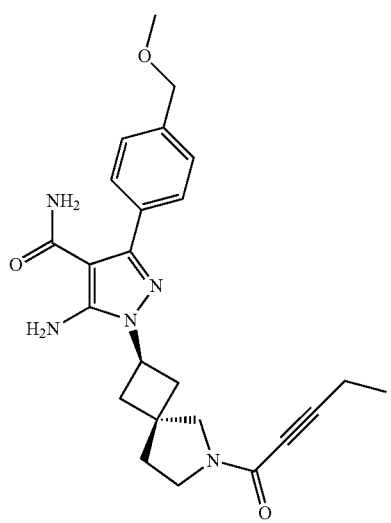
13
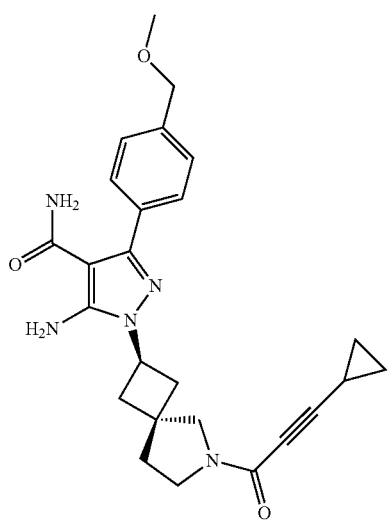
14
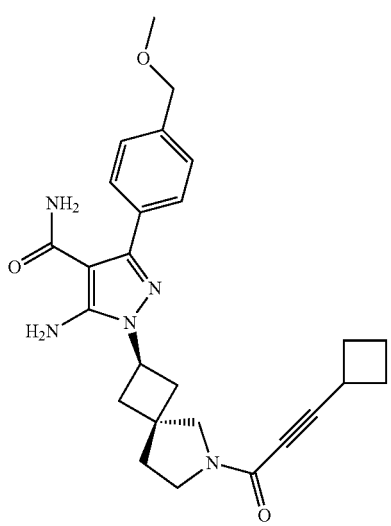

15
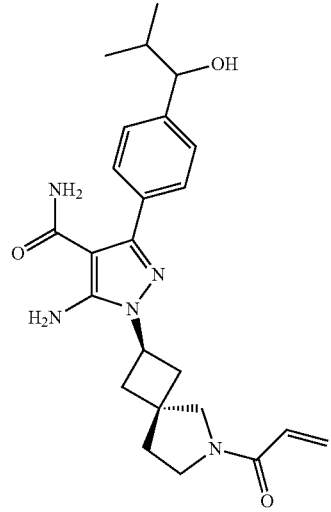
16
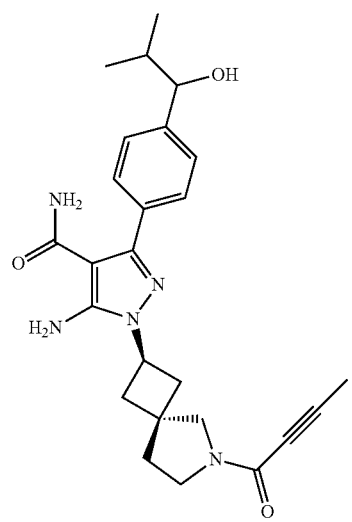
17
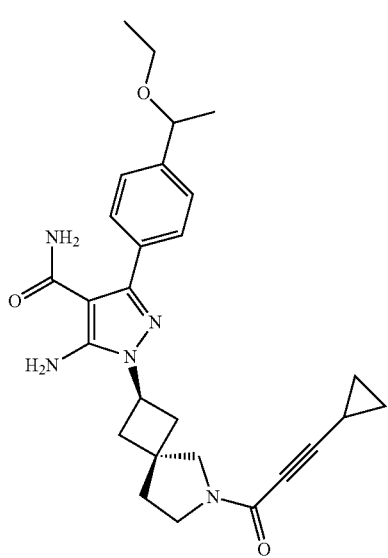
18
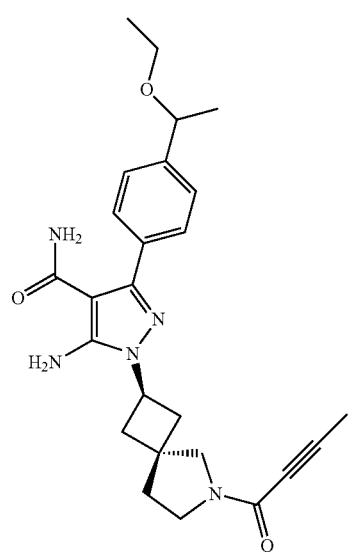
19
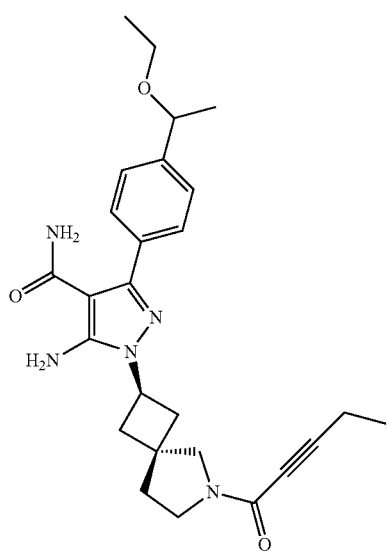
20
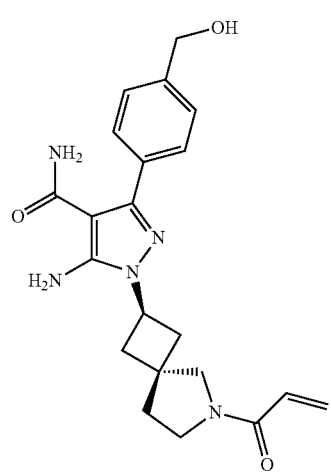

21
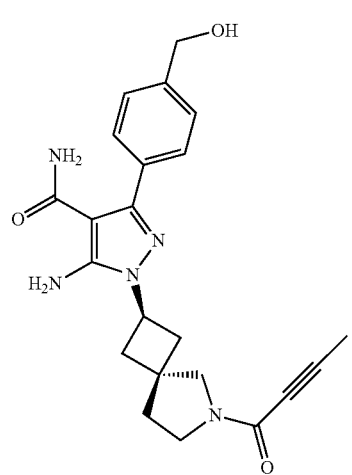
22
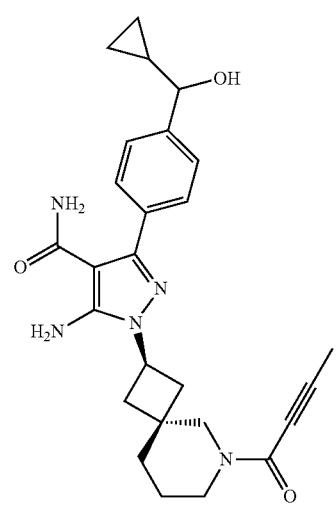
23
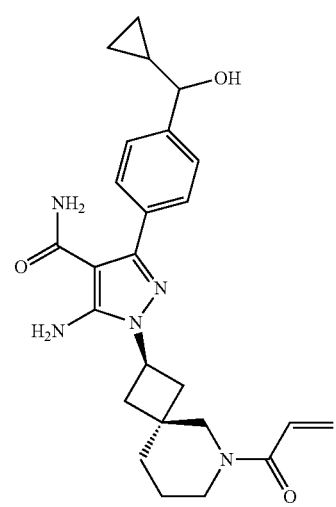
24
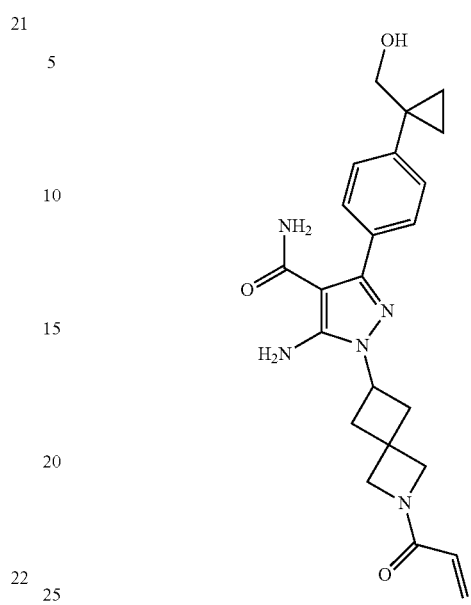
25
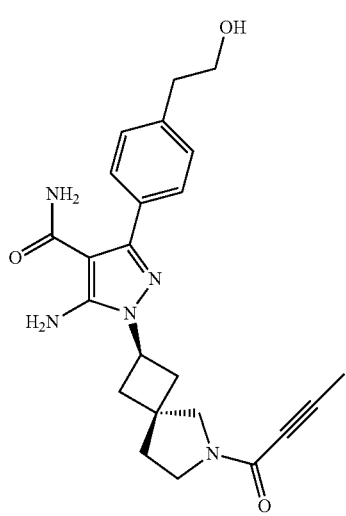
26
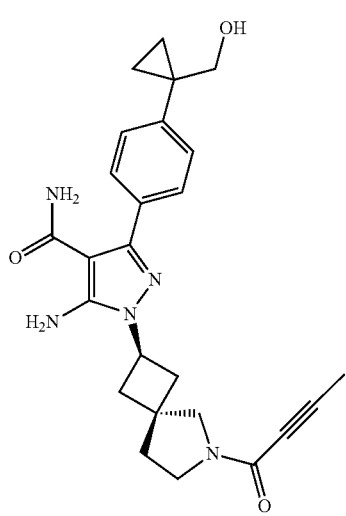

-continued

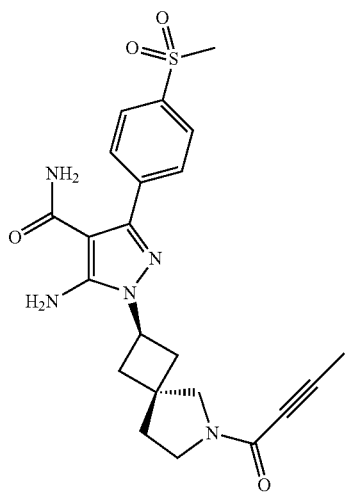

or a pharmaceutically acceptable salt thereof.

6. A pharmaceutical composition comprising a therapeutically effective amount of a compound according to claim 1 or a pharmaceutically acceptable salt thereof.

7. A method of treating a disease chosen from rheumatoid arthritis, systemic lupus erythromatosis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis, comprising administering to a patient a therapeutically effective amount of a compound according to claim 1 or a pharmaceutically acceptable salt thereof.

* * * * *